United States Patent [19]

Carethers et al.

[11] Patent Number: 4,868,200

[45] Date of Patent: Sep. 19, 1989

[54] NOVEL ENOLAMIDES, PHARMACEUTICAL COMPOSITIONS AND METHODS OF USE THEREOF FOR ACTIVITY AS MODULATORS OF THE ARACHIDONIC ACID CASCADE

[75] Inventors: Mary E. Carethers, Cincinnati, Ohio; Wiaczeslaw A. Cetenko; David T. Connor, both of Ann Arbor, Mich.; Elizabeth A. Johnson, Corte Madera, Calif.; John S. Kiely, Ann Arbor, Mich.; Charles F. Schwender, Califon, N.J.; Jagadish C. Sircar, Ann Arbor, Mich.; Roderick J. Sorenson, Ann Arbor, Mich.; Paul C. Unangst, Ann Arbor, Mich.; Robert F. Bruns, Ann Arbor, Mich.

[73] Assignee: Warner-Lambert Company, Morris Plains, N.J.

[21] Appl. No.: 166,146

[22] Filed: Mar. 9, 1988

Related U.S. Application Data

[62] Division of Ser. No. 121,264, Nov. 16, 1987, which is a division of Ser. No. 782,623, , Pat. No. 4,761,424.

[51] Int. Cl.$^4$ .................... A61K 31/40; C07D 209/36
[52] U.S. Cl. .................................. 514/418; 514/411; 548/450; 548/484
[58] Field of Search ................ 548/484, 450; 514/418, 514/411

[56] References Cited

PUBLICATIONS

Chem. Abstracts; Goerlitzer, vol. 93; 204495v (1980).

*Primary Examiner*—Mary C. Lee
*Assistant Examiner*—Johann Richter
*Attorney, Agent, or Firm*—Joan Thierstein

[57] ABSTRACT

The present invention relates to novel enolamide type compounds, pharmaceutical compositions, and methods of use thereof, useful in the treatment of diseases in which products of lipoxygenase enzyme activity or the action of leukotrienes contribute to the pathological condition.

16 Claims, No Drawings

NOVEL ENOLAMIDES, PHARMACEUTICAL COMPOSITIONS AND METHODS OF USE THEREOF FOR ACTIVITY AS MODULATORS OF THE ARACHIDONIC ACID CASCADE

This application is a divisional of U.S. Ser. No. 121,264 filed Nov. 16, 1987, which is a divisional of U.S. Ser. No. 782,623 filed Oct. 1, 1985, now U.S. Pat. No. 4,761,424.

BACKGROUND OF THE INVENTION

The present invention relates to novel compounds, pharmaceutical compositions, and methods of use for the treatment of diseases in which products of lipoxygenase enzyme activity or the action of leukotrienes contribute to the pathological condition. The novel compounds of the present invention have activity useful for treating asthma, allergies, cardiovascular diseases, migraines, and immunoinflammatory conditions. Selected novel intermediates are also the present invention.

More particularly, this invention concerns certain novel enolamides having the Formula I as defined below, pharmaceutical compositions having the novel enolamides therein, and methods of use therefor in the treatment or amelioration of diseases in which products of lipoxygenase enzyme activity or the reaction of leukotrienes contribute to the pathological condition. That is, the novel enolamides inhibit lipoxygenase and/or bind leukotriene receptors. Lipoxygenase enzymes are well known in the arachidonic acid cascade.

Arachidonic acid serves as the biological precursor for a family of physiologically active eicosanoids. These include products derived from the action of cyclooxygenase such as the class of prostaglandin-E and -F compounds, thromboxanes, and prostacyclin, and products derived from the action of lipoxygenase enzymes such as hydroxy- and hydroperoxyeicosatetraenoic acids and the leukotrienes.

Lipoxygenase pathway products such as leukotrienes B4, C4, D4, and E4, 5-hydroxyeicosatetraenoic acid, 5-hydroperoxyeicosatetraenoic acid, and 12-hydroxyeicosatetraenoic acid are related to the condition recognized as inflammation, and in allergic and immune responses.

These lipoxygenase products have been shown to be highly potent stereospecific inducers of polymorphonuclear leukocyte migration or chemotaxis, lysosomal enzyme release, and degranulation. Additionally, these products induce the contraction of smooth muscle such as vascular and pulmonary tissue, and induce the generation of additional inflammogens such as thromboxane A2 and prostacyclin. Lipoxygenase products also interact with vasodilator prostanoids and other mediators, leading to the enhancement or amplification of the inflammatory response.

Leukotrienes and the hydroxy- and hydroperoxyeicosatetraenoic acids play a major role in the pathogenesis of many disease conditions. These compounds have been found in synovial fluid of rheumatoid joints, in involved skin of psoriatic patients, in inflamed colonic tissue, and at elevated levels in ischemic myocardial tissue. They are also mediators of allergic and asthmatic conditions.

Compounds and pharmaceutical compositions in accordance with the present invention inhibit lipoxygenase or the biosynthesis or biochemical action of leukotrienes and, therefore, are useful in the treatment or amelioration of a number of diseases whose pathogenesis involves the production of the leukotrienes and other lipoxygenase-derived products. These lipoxygenase inhibitors aid in the prevention of tissue damage and inflammation which result from infiltration of leukocytes, release of tissue-digesting lysosomal enzymes, and changes in the permeability and contractile state of smooth muscle tissue.

Specific conditions in which such lipoxygenase-inhibiting or leukotriene-antagonizing compounds and pharmaceutical compositions in accordance with the present invention are useful include allergy; asthma; arthritis; skin disorders including psoriasis and acne; inflammation; inflammatory bowel diseases; pain; and cardiovascular disorders including myocardial ischemia and infarction, angina, arrhythmias, stroke, and atherosclerosis.

Among the novel enolamides of the present invention are benzothiopyrans and oxides thereof of Formula I having a moiety, Q, shown as substituent $I_1$; benzothiazine, 1,1-dioxide type compounds having a moiety, Q, shown as substituent $I_2$; benzofurans having a moiety, Q, shown as substituent $I_3$; benzo[b]thiophenes having a moiety, Q, shown as substituent $I_4$; benzopyrans having a moiety, Q, shown as substituent $I_5$; furo[3,2-b]indoles having a moiety, Q, shown as substituent $I_6$; and indole amides having a moiety, Q, shown as substituent $I_7$. Definitions for the various moieties of the present invention are found in the subsequent descriptions herein.

Of the above defined enolamides the compounds of Formula I wherein Q is $I_1$ and wherein Q is $I_4$ are found to have leukotriene receptor affinities also described herein as leukotriene antagonists.

Specific aryl carboxamides of benzothiopyran dioxides useful as antiinflammatory agents are described in British Pat. No. 1,338,996 including an aryl amide having aryl as a naphthyl radical or an aryl substituted by among others alkyl, aryl, or aralkyl. Additionally, U.S. Pat. No. 3,828,073 describes phenyl carboxamides of benzothiopyrans and their corresponding S-oxides also having an antiinflammatory utility. This patent includes the phenyl having specific alkyl, aryl, and aralkyl substituents.

The dioxides of benzothiazines having various carboxamide moieties also useful as antiinflammatory agents are disclosed in U.S. Pat. Nos. 3,591,584; 3,674,876; 3,803,205; 3,862,319; 3,891,637; 3,892,740; 3,900,470; and 3,923,801 and also in British Pat. No. 2,118,544; Belgian Pat. No. 751,300; and Japanese No. 58225-076. Among the various carboxamides are naphthyl and substituted phenyl carboxamides including as phenyl substituents, an alkyl group.

U.S. Pat. No. 3,646,020 includes a lower alkyl substituted phenyl carboxamide as an intermediate. Lombardino et al, "Synthesis and Antiinflammatory Activity of Some 3-Carboxamides of 2-Alkyl-4-hydroxy-2H-1,2-benzothiazine 1,1-dioxide," *J. of Medicinal Chem.*, Vol. 14, No. 12, pp 1171–1175 (1971) discloses naphthyl carboxamide and lower alkyl substituted phenyl carboxamides. Zinnes et al, "1,2-benzothiazines, $6^1$,3-carbamoyl-4-hydroxy-2H-1,2-benzothiazine-1,1-dioxides as Antiinflammatory Agents," *J. of Medicinal Chemistry*, Vol. 16, No. 1, pp 44–48 (1973) discloses phenyl substituted phenyl carboxamides.

Selected enolic benzofuran amides are disclosed by M. Pesson and M. Joannic, "New Derivatives of 2-carboxamido-3-hydroxybenzofuran" and in British Pat. No. 1,233,268 having choleretic activity.

Enolic indole amides generally are known. See M. Saxena and S. R. Ahmed, *J. Med. Chem.*, 12, 1120 (1969). However, the compounds of the present Formula I are not suggested by the limited disclosure of such known amides.

Also falling within the scope of the present invention are the pharmaceutically acceptable acid and base addition salts of the compounds of the present invention.

SUMMARY OF THE INVENTION

The present invention are compounds of the Formula I and pharmaceutically acceptable salts thereof wherein:

(1) y is one or two (2) Q is a substituent selected from the group consisting of the Formula $I_1$, $I_2$, $I_3$, $I_4$, $I_5$, $I_6$, and $I_7$ wherein a is zero, one or two; b is zero, one, two, three or four; X and Z are each independently hydrogen or lower alkyl; $R_1$ may be the same or different if b is two or more and is selected from a group consisting of alkyl of from one to four carbons, inclusive, alkoxy of from one to four carbons, inclusive, carboalkoxy of from two to four carbons, inclusive, hydroxy, halogen, nitro, acyl of from two through four carbons, inclusive, acylamino, of from two through four carbons, inclusive, amino, mono- and di-alkylaminohaving each alkyl the same or different from one to four carbons, inclusive, carboalkoxyamido, of from one to four carbons, inclusive, alkylsulfonamido of from one to four carbons, inclusive, alkylsulfinyl of from one to four carbons, inclusive, alkylsulfonyl of from one to four carbons, inclusive, and where a is one then $R_1$ may also be —(CH=CH—CH=CH)— taken together with adjacent ring carbons to form a benzo radical; $R_2$ and $R_3$ are the same or different and are hydrogen, alkyl of from one to six carbons, inclusive, phenyl or benzyl;

(3) $R_5$ is hydrogen; alkyl of from one to four carbons, inclusive; alkoxy of from one to four carbons, inclusive; carbalkoxy of from two to four carbons, inclusive; hydroxy, halogen, or —(CH=CH—CH=CH)— taken together with adjacent carbons to form a benzo radical;

(4) $R_6$ is (a) alkyl of from six to twenty carbons, (b) —CH=CH—$R_4$, (c) —(CH$_2$)$_n$CO$R_4$, or (d) —(CH$_2$)$_n$—$R_4$ wherein n is zero to four, inclusive, and $R_4$ is phenyl optionally substituted at the two through six positions by alkyl of from one to four carbons, inclusive, lower alkoxy carbonyl, carbalkoxy having alkoxy of from one to four carbons, inclusive, alkoxy or thioalkoxyl of from one to four carbons, inclusive, phenalkoxy, amino, monoalkyl- or dialkylamino having the alkyl of from one to four carbons, inclusive, alkanoylamino of from two to six carbons, inclusive, carboxyl, halogen, hydroxy, hydroxyalkyl of from one to four carbons, inclusive, alkanoyl of from one to four carbons, inclusive, nitro, alkanesulfonamido of from one to four carbons, or phenyl; and with the proviso that when Q is $I_1$ or $I_2$ having y as one then $R_6$ cannot be alkyl, $R_4$ cannot be phenyl in —(CH$_2$)$_n$—$R_4$ and $R_5$ cannot be —(CH=CH—CH=CH)— taken together with adjacent carbons to form a benzo radical.

The embodiments of the present invention are compounds of Formula I wherein Q is (a) $I_1$, (b) $I_2$, (c) $I_3$, (d) $I_4$, (e) $I_5$, (f) $I_6$, or (g) $I_7$, all having the above definitions.

One group of preferred compounds of Formula I include compounds wherein $R_1$, $R_2$, $R_5$ is hydrogen or the benzo radical, and X and Z are hydrogen, a is 2, y is 1, and $R_6$ is alkyl of from 6 to 20 carbons, inclusive, or —(CH$_2$)$_n$$R_4$ wherein n is two and $R_4$ is phenyl optionally substituted by alkyl of from one to four carbons, inclusive, carboxyl, carboalkoxy of from one to four carbons, inclusive, chloro, alkoxy of from one to four carbons, inclusive, hydroxy, or phenyl; or the pharmaceutically acceptable acid or base addition salts thereof.

Another group of preferred compounds of Formula I include compounds wherein $R_1$ and $R_2$ are hydrogen, y is 2, $R_5$ is hydrogen or the benzo radical; $R_6$ is alkyl of from 6 to 20 carbons, inclusive, or —(CH$_2$)$_n$—$R_4$ wherein n is 2 and $R_4$ is phenyl optionally substituted by alkyl of from one to four carbons, inclusive, lower alkoxycarbonyl; carboxyl, carboalkoxy wherein the alkoxy is from one to four carbons, inclusive, alkoxy of from one to four carbons, inclusive, hydroxy; or pharmaceutically acceptable acid or base addition salts.

Thus, the more preferred compounds of Formula I are:

2H-1,2-Benzothiazine-3-carboxamide, N-[4-[2-(3,4-dihydroxyphenyl)ethyl]phenyl]-4-hydroxy-2-methyl-1,1-dioxide.

2H-1,2-Benzothiazine-3-carboxamide, N-[4-[2-(3,4-dihydroxyphenyl)ethyl]phenyl]-4-hydroxy-2-methyl-1,1-dioxide, compound with methanol (4:1).

2H-1,2-Benzothiazine-3-carboxamide, N-[4-[2-(3,4-dihydroxyphenyl)ethyl]phenyl]-4-hydroxy-2-methyl-1,1-dioxide, L-arginate (salt) (1:1).

Benzo[b]thiophene-2-acetamide, N-[4-[2-(3,4-dimethoxyphenyl)ethyl]phenyl]-3-hydroxy-α-oxo.

Benzo[b]thiophene-2-acetamide, N-[4-[2-(3,4-dihydroxyphenyl)ethyl]phenyl]-3-hydroxy-α-oxo.

Benzo[b]thiophene-2-acetamide, N-[4-[2-(3,4-dihydroxyphenyl)ethyl]phenyl]-3-hydroxy-α-oxo, compound with 1-piperidineethanol (1:1).

2H-1-Benzothiopyran-3-carboxamide, 3,4-dihydro-4-oxo-N-[4-[2-[4-(trifluoromethyl)phenyl]ethyl]phenyl]-1,1-dioxide.

2H-Furo[3,2-b]indole-2-carboxamide, N-[4-[2-(3,4-dihydroxyphenyl)ethyl]phenyl]-3,4-dihydro-7-hydroxy-3-oxo-4-phenyl.

Naphtho[2,3-b]furan-2-carboxamide, N-[4-[2-(3,4-dihydroxyphenyl)ethyl]phenyl]-3-hydroxy.

2H-1-Benzothiopyran-3-carboxamide, 4-hydroxy-N-[4-[2-(2-naphthalenyl)ethyl]phenyl], 1,1-dioxide.

2H-1-Benzothiopyran-3-carboxamide, N-[4-[2-(3,4-dihydroxyphenyl)ethyl]phenyl]-4-hydroxy-, 1,1-dioxide.

1H-Indole-2-acetamide, N-[4-[2-(3,4-dihydroxyphenyl)ethyl]phenyl]-3-hydroxy-5,6-dimethyl-α-oxo.

2H-1-Benzopyran-3-acetamide, N-[4-[2-(3,4-dihydroxyphenyl)ethyl]phenyl]-4-hydroxy-α-oxo.

2H-1-Benzothiopyran-3-carboxamide, N-[4-[2-(4-butoxyphenyl)ethyl]phenyl]-3,4-dihydro-4-oxo-1,1-dioxide.

2H-1-Benzothiopyran-3-acetamide, N-(4-decylphenyl)-4-hydroxy-α-oxo.

Naphtho[2,1-b]furan-2-carboxamide, 1-hydroxy-N-[4-[2-(3,4-dimethoxyphenyl)ethyl]phenyl].

Naphtho[2,1-b]furan-2-carboxamide, N-[4-[2-(3,4-dihydroxyphenyl)ethyl]phenyl]-1-hydroxy.

2H-1-Benzothiopyran-3-carboxamide, N-[4-[2-(3,4-dichlorophenyl)ethyl]phenyl]-3,4-dihydro-4-oxo-1,1-dioxide.

Benzo[b]thiophene-2-acetamides, N-[4-[2-(3,4-dichlorophenyl)ethyl]phenyl]-3-hydroxy-α-oxo.

2-Benzofuranacetamide, N-[4-[2-(3,4-dichlorophenyl)ethyl]phenyl]-2,3-dihydro-α3-dioxo.

2H-1,2-Benzothiazine-3-carboxamide, N-[4-[2-(3,4-dichlorophenyl)ethyl]phenyl]-4-hydroxy-2-hydroxy-2-methyl-1,1-dioxide.

Naphth[2,3-b]furan-2-acetamide, N-[4-[2-(3,4-dichlorophenyl)ethyl]phenyl]3-hydroxy-α-oxo.

Benzo[b]thiophene-2-acetamide, 3-hydroxy-N-[4-[2-(4-hydroxy-3-methoxyphenyl)ethyl]phenyl]-α-oxo.

2H-1-Benzothiopyran-3-carboxamide, 4-hydroxy-N-[4-[2-(4-hydroxy-3-methoxyphenyl)ethyl]phenyl]-1,1-dioxide.

However compounds of Formula I embodied by each of $I_1$, $I_2$, $I_3$, $I_4$, $I_5$, $I_6$, and $I_7$ contain preferred, more preferred, and/or most preferred compounds and are, therefore, each discussed separately.

The most preferred compounds of Formula I wherein Q is $I_1$ include the following species:

N-[4-[2-(3,4-dihydroxyphenyl)ethyl]phenyl]-3,4-dihydro-4-oxo-2H-1-benzothiopyran-3-carboxamide, 1,1-dioxide.

N-[4-[2-(3,4-dichlorophenyl)ethyl]phenyl]-3,4-dihydro-4-oxo-(2H)-1-benzothiopyran-3-carboxamide-1,1-dioxide.

N-[4[2-(4-biphenyl)ethyl]phenyl]-3,4-dihydro-4-oxo-(2H)-1-benzothiopyran-3-carboxamide-1,1-dioxide.

N-[4-[2-(3,4-dimethoxyphenyl)ethyl]phenyl]-3,4-dihydro(2H)-1-benzothiopyran-3-carboxamide-1,1-dioxide.

N-[4-(n-decyl)phenyl]-3,4-dihydro-4-oxo(2H)-1-benzothiopyran-3-carboxamide-1,1-dioxide.

N-[4-(n-decyl)phenyl]acetamide-3,4-dihydro-4-oxo-(2H)-1-benzothiopyran-α-oxo-1,1-dioxide.

N-[4-[2-(4-chlorophenyl)ethyl]phenyl]-3,4-dihydro-4-oxo-2H-1-benzothiopyran-3-carboxamide, 1,1-dioxide.

N-[4-[2-(3,4-dihydroxyphenyl)ethyl]phenyl]-4-hydroxy-2H-1-benzothiopyran-3-carboxamide, 1,1-dioxide.

4-Hydroxy-4-[2-(2-naphthalenyl)ethyl]phenyl]-2H-1-benzothiopyran-3-carboxamide, 1,1-dioxide.

N-[4-[2-(3,4-dimethylphenyl)ethyl]phenyl]-3,4-dihydro-4-oxo-2H-1-benzothiopyran-3-carboxamide, 1,1-dioxide.

N-[4-[2-(3-trifluoromethylphenyl)ethyl]phenyl]-4-hydroxy-2H-1-benzothiopyran-3-carboxamide, 1,1-dioxide.

4-hydroxy-N-[4-[2-(4-hydroxy-3-methoxyphenyl)ethyl]phenyl]-2H-1-benzothiopyran-3-carboxamide, 1,1-dioxide.

N-[4-[2-(2,4-dichlorophenyl)ethyl]phenyl]-4-hydroxy-2H-1-benzothiopyran-3-carboxamide, 1,1-dioxide.

N-[3-[2-(3,4-dichlorophenyl)ethyl]phenyl]-4-hydroxy-2H-1-benzothiopyran-3-carboxamide, 1,1-dioxide.

N-[4-[3-(3,4-dichlorophenyl)propyl]phenyl]-4-hydroxy-2H-1-benzothiopyran-3-carboxamide, 1,1-dioxide.

Most preferred compound of Formula I wherein Q is $I_2$ are:

N-[4-[2-(3,4-dimethoxyphenyl)ethyl]phenyl]-4-hydroxy-2-methyl-2H-1,2-benzothiazine-3-carboxamide, 1,1-dioxide.

N-[4-[2-(3,4-dihydroxyphenyl)ethyl]phenyl]-4-hydroxy-2-methyl-2H-1,2-benzothiazine-3-carboxamide, 1,1-dioxide.

N-[4-[2-(3,4-dihydroxyphenyl)ethyl]phenyl]-4-hydroxy-2H-1,2-benzothiazine-3-carboxamide, 1,1-dioxide.

N-[2-[2-(3,4-dimethoxyphenyl)ethyl]phenyl]-4-hydroxy-2-methyl-2H-1,2-benzothiazine-3-carboxamide-1,1-dioxide.

N-[2-[2-(3,4-dihydroxyphenyl)ethyl]phenyl]-4-hydroxy-2-methyl-2H-1,2-benzothiazine-3-carboxamide, 1,1-dioxide.

N-(4-decylphenyl)-4-hydroxy-2-methyl-2H-1,2-benzothiazine-3-carboxamide, 1,1-dioxide.

N-[4-[2-(3,4-dichlorophenyl)ethyl]phenyl]-4-hydroxy-2-methyl-2H-1,2-benzothiazine-3-carboxamide, 1,1-dioxide.

Compounds of Formula I wherein Q is $I_2$ which are preferred include:

2H-1,2-Benzothiazine-3-carboxamide, 4-hydroxy-N-[4-[2-(4-hydroxy-3-methoxyphenyl)ethyl]phenyl]-2-methyl-, 1,1-dioxide, and 2H-1,2-Benzothiazine-3-carboxamide, 4-hydroxy-N-[4-[2-(4-hydroxy-3-methoxyphenyl]ethenyl]phenyl]-2-methyl-, 1,1-dioxide.

More preferred compounds of Formula I wherein Q is $I_3$ are:

2-Benzofuranacetamide, N-[4-[2-(3,4-dihydroxyphenyl)ethyl]phenyl]-2,3-dihydro-α,3-dioxo-;

2-Benzofuranacetamide, N-[4-[2-(3,4-dimethoxyphenyl)ethyl]phenyl]-3-hydroxy-αoxo-;

2-Benzofuranacetamide, N-[4-[2-(3,4-dihydroxyphenyl)ethyl]phenyl]-3-hydroxy-7-methoxy-αoxo-, 2-Benzofurancarboxamide, N-[4-[2-(3,4-dihydroxyphenyl)ethyl]phenyl]-3-hydroxy-;

2-Benzofuranacetamide, N-[4-[2-(3,4-dichlorophenyl)ethyl]phenyl]-2,3-dihydro-α,3-dioxo-;

Naphtho[2,3-b]furan-2-acetamide, N-[4-[2-(3,4-dichlorophenyl)ethyl]phenyl]-3-hydroxy-α-oxo-.

The most preferred compounds of Formula I wherein Q is $I_3$ are:

Naphtho[2,3-b]furan-2-carboxamide, N-[4-[2-(3,4-dimethoxyphenyl]ethyl]phenyl]-2,3-dihydro-3-oxo;

Naphtho[2,3-b]furan-2-carboxamide, N-[4-[2-(3,4-dihydroxyphenyl]ethyl]phenyl]-3-hydroxy;

Naphtho[2,1-b]furan-2-carboxamide, N-[4-[2-(3,4-dimethoxyphenyl]ethyl]phenyl-1-hydroxy;

Naphtho[2,1-b]furan-2-carboxamide, N-[4-[2-(3,4-dihydroxyphenyl]ethyl]phenyl-1-hydroxy;

Naphtho[1,2-b]furan-2-carboxamide, N-[4-[2-(3,4-dihydroxyphenyl]ethyl]phenyl-3-hydroxy;

Naphtho[2,1-b]furan-2-carboxamide, N-[4-[2-(4-hydroxy-3-methoxyphenyl)ethyl]phenyl-1,2-dihydro-1-oxo.

Most preferred compounds of Formula I wherein Q is $I_4$ are:

Benzo[b]thiophene-2-acetamide, N-[4-[2-(3,4-dimethoxyphenyl)ethyl]phenyl]-3-hydroxy-α-oxo-;

Benzo[b]thiophene-2-acetamide, N-[4-[2-(3,4-dihydroxyphenyl)ethyl]phenyl]-3-hydroxy-α-oxo-;

Benzo[b]thiophene-2-carboxamide, N-[4-[2-(3,4-dimethoxyphenyl)ethyl]phenyl]-3-hydroxy-;

Benzo[b]thiophene-2-carboxamide, N-[3-[2-(3,4-dichlorophenyl)ethyl]phenyl]-3-hydroxy-.

Most preferred compounds of Formula I wherein Q is $I_5$ are:

N-[4-[2-(3,4-dihydroxyphenyl)ethyl]phenyl]-4-hydroxy-α-oxo-2H-1-benzopyran-3-acetamide;

More preferred compounds of Formula I wherein Q is $I_6$ are:

2H-Furo[3,2-b]indole-2-carboxamide, N-[4-[2-(3,4-dihydroxyphenyl)ethyl]phenyl]-3,4-dihydro-3-oxo-4-phenyl.

2H-Furo[3,2-b]indole-2-carboxamide, N-[4-[2-(4-methoxyphenyl)ethyl]phenyl]-3,4-dihydro-4-methyl-3-oxo.

2H-Furo[3,2-b]indole-2-carboxamide, N-[4-[2-(4-hydroxyphenyl)ethyl]phenyl]-3,4-dihydro-4-methyl-3-oxo.

2H-Furo[3,2-b]indole-2-acetamide, N-[4-[2-(3,4-dimethoxyphenyl)ethyl]phenyl]-3,4-dihydro-4-methyl-$\alpha$,3-dioxo.

2H-Furo[3,2-b]indole-2-acetamide, N-[4-[2-(3,4-dihydroxyphenyl)ethyl]phenyl]-3,4-dihydro-4-methyl-$\alpha$,3-dioxo.

2H-Furo[3,2-b]indole-2-acetamide, N-[4-[2-(3,4-dimethoxyphenyl)ethyl]phenyl]-3,4-dihydro-7-methoxy-$\alpha$,3-dioxo-4-phenyl.

Most preferred compounds of Formula I wherein Q is $I_6$ are:

4H-Furo[3,2-b]indole-2-carboxamide, N-[4-[2-(3,4-dihydroxyphenyl)ethyl]phenyl]-3-hydroxy-4-methyl;

4H-Furo[3,2-b]indole-2-carboxamide, N-[4-[2-(3,4-dimethoxyphenyl)ethyl]phenyl]-3-hydroxy-4-methyl;

2H-Furo[3,2-b]indole-2-carboxamide, N-[4-[2-(3,4-dimethoxyphenyl)ethyl]phenyl]-3,4-dihydro-7-methoxy-3-oxo-4-phenyl;

2H-Furo[3,2-b]indole-2-carboxamide, N-[4-[2-(3,4-dihydroxyphenyl)ethyl]phenyl]-3,4-dihydro-7-hydroxy-3-oxo-4-phenyl;

2H-Furo[3,2-b]indole-2-acetamide, N-[4-[2-(3,4-dihydroxyphenyl)ethyl]phenyl]-3,4-dihydro-7-hydroxy-$\alpha$,3-dioxo-4-phenyl.

More preferred compounds of Formula I wherein Q is $I_7$ are:

1H-Indole-2-carboxamide, N-[4-[2-(3,4-dihydroxyphenyl)ethyl]phenyl]-3-hydroxy-1-methyl;

1H-Indole-2-acetamide, N-[4-[2-(3,4-dimethoxyphenyl)ethyl]phenyl]-3-hydroxy-5,6-dimethyl-$\alpha$-oxo;

1H-Indole-2-acetamide, N-(4-decylphenyl)-3-hydroxy-5,6-dimethyl-$\alpha$-oxo;

1H-Indole-2-carboxamide, N-[4-[2-(3,4-dihydroxyphenyl)ethyl]phenyl]-3-hydroxy;

1H-Indole-2-acetamide, N-[4-[2-(3,4-dihydroxyphenyl)ethyl]phenyl]-3-hydroxy-5,6-dimethyl-$\alpha$-oxo.

The compounds of the present invention include certain substituted 4-oxo- or 4-hydroxy-benzothiazine-3-carboxamide, 1,1-dioxides. Although depicted in the enol form, with a hydroxy group at respective positions in $I_1$, $I_2$, $I_3$, $I_4$, $I_5$, $I_6$, and $I_7$ within the structural Formula I above, compounds of the present invention are capable of existence in both the keto and enol tautomeric forms. The compounds may thus, for example, be named as either 3,4-dihydro-4-oxo-2H-1-benzothiazine-3-carboxamides in the keto form or as 4-hydroxy2H-1-benzothiazine-3-carboxamides in the enol form, and may be depicted in structural formulae in either form. The present invention contemplates both forms of the compounds, and the two forms are considered equivalent for purposes of the present invention.

The present invention is also a pharmaceutical composition comprising an effective amount of a compound having the Formula I as defined above together with a pharmaceutically acceptable carrier. An effective amaount is the amount useful for treating or ameliorating a number of diseases or conditions comprising an inhibition of a lipoxygenase effect or comprising a binding of a leukotriene receptor. The diseases or conditions are readily recognized for the pathogenesis affected by the inhibitory lipoxygenase effect and affected by the binding of a leukotriene receptor, as recited herein.

Thus, in accordance with the present invention, another aspect of the invention, provides a method of administering to mammals, including humans, in need of treatment or amelioration of diseases or conditions an amount effective for treatment of the diseases or conditions of a compound or composition having the Formula I as defined above. The need is evident for diseases or conditions benefiting from inhibition of a lipoxygenase effect.

By virtue of the activity of the compounds having the Formula I of the present invention as leukotriene D4 antagonists, and inhibitors of 5-lipoxygenase and histamine release from basophils the compounds are useful in treating asthmas and allergies as well as cardiovascular disorders, migraine, and immunoinflammatory conditions. See B. Samulesson, "Leukotrienes: Mediators of Immediate Hypersensitivity Reactions and Inflammation, "*Science*" Vol. 220, p 568 (1983); P. J. Piper, "Leukotrienes," *Trends in Pharmaceutic Sciences*, pp 75 & 77 (1983), and J. L. Romson, et al, "Reduction of the Extent of Ischemic Myocardial Injury by Neutrophil Depletion in the Dog," *Circulation*, Vol. 67, pp 1016 (1983).

Additionally, the activity, of the compounds having the Formula I of the present invention is determined by the well known leukotriene receptor binding assay that is described by R. F. Bruns, W. J. Thomsen and T. A. Pugsley in *Life Sciences*, 33, 645 (1983) or the Herxheimer in vivo antiallergy test described in H. Herxheimer, *J. Physiol.* (London), Vol. 177, p. 251 (1952).

The antiasthma and antiallergic activity provides methods of treatment for hypersensitivity reaction having broad symptoms. For example, the symptoms may include dermatitis, lacrimation, nasal discharge, coughing, sneezing, nausea, vomiting, diarrhea, difficulty in breathing, pain, inflammation, and in severe cases, anaphylatic shock and circulatory collapse. The symptoms may be found in man as well as other animals suffering from bronchial asthma, seasonal pollinosis (e.g., hayfever), allergic rhinitis, urticoria, allergic conjunctivitis, food allergies, and anaphylactoid reactions.

Likewise, the activity of the compounds of Formula I provides a method of treatment for cardiovascular disorders, particularly ischemia and myocardial infarctions. The symptoms of a subject having a cardiovascular disorder may be determined by special diagnostic procedures directed to subjects having a history, general physical appearance and then detailed deviations from normal appearance suggesting a cardiovascular disorder. Such disorders are also found in man as well as other mammals. Symptoms of the disorders are described extensively in *The Merck Manual* 14th ed, (1982).

Further, method of treatment is provided by the compounds of Formula I herein for migraine and inflammation. The symptoms requiring treatment for these purposes are also readily recognized, particularly for migraine in man and/or inflammation in man as well as other mammals.

Pharmaceutical compositions which also are the present invention are prepared from the compound of Formula I and salts thereof described as the present invention having inert pharmaceutical carriers. The compositions may be either solid or liquid.

A physician or veterinarian of ordinary skill readily determines a subject who is exhibiting symptoms described herein. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an affected area (e.g., in the form of eye drops or by inhalation). For the treatment of asthma or allergies such as erythema, the compounds of the present invention may also be administered topically in the form of ointments, creams, gels, or the like. However, in general, the preferred route of administration is orally.

An effective but nontoxic quantity of the compound is employed in treatment. The ordinarily skilled physician or veterinarian will readily determine and prescribe the effective amount of the compound to prevent or arrest the progress of the condition for which treatment is administered. In so proceeding, the physician or veterinarian could employ relatively low dosages at first, subsequently increasing the dose until a maximum response is obtained.

Initial dosages of the compounds of the invention having Formula I are ordinarily in the area of 1 mg up to 3 g per day orally, preferably 1 mg to 500 mg per dose orally, given from one to four times daily or as needed. When other forms of administration are employed equivalent doses are administered.

The compounds of the invention are capable of forming both pharmaceutically acceptable acid addition and/or base salts. Base salts are formed with metals or amines, such as ammonium, alkali, and alkaline earth metals or organic amines. Examples of metals used as cations are sodium, potassium, magnesium, calcium, and the like. Examples of suitable amines are N,N'dibenzylethylenediamine, chloroprocaine, choline, diethanolamine, ethylenediamine, N-methylflucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicyclic, malic, gluconic, fumaric, succinic, ascorbic, maleic, methanesulfonic, arginine, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, including hydrated forms and the like are equivalent to the unsolvated forms for purposes of the invention.

Finally, the methods of preparation and selected novel intermediates for preparation for compounds of Formula I as defined above are also the present invention.

Generally, a method of preparation of the compounds of Formula I as defined above can be accomplished as shown in Scheme I wherein Q, y, $R_5$, and $R_6$ are as defined above and R is hydrogen, lower alkyl, or phenyl.

When R is hydrogen the preparation of the compound of Formula I shown in Scheme I may be accomplished by reacting the acid II wherein R is hydrogen with dicyclohexylcarbodiimide or carbonyldiimidazole and the desired compound of Formula III in an inactive solvent, such as tetrahydrofuran, methylene chloride or ethylene dichloride or mixtures thereof under nitrogen at from about $-10°$ C. to about room temperature for from 50 minutes to 24 hours. Optimum conditions vary within reasonable experimentation depending upon the reactants.

Alternatively, when R is lower alkyl or phenyl the preparation of the compound of Formula I shown in Scheme I may be accomplished by reacting the ester II wherein R is lower alkyl or phenyl in the presence of butyl lithium, diisopropylamine, and the desired aniline of Formula III. An inert organic solvent such as tetrahydrofuran is used in the reaction which is maintained at ice bath temperature with an ice bath for from ten minutes to two hours. See, for example, K. W. Yank, et al, *Tetrahedron Letters*, 1791 (1970).

Specific variations within the above general description may include, for example, preparation of compounds of Formula I wherein $R_4$ includes phenyl optionally substituted by at least one hydroxy group by treatment of corresponding methoxy groups to replace the methyl by hydrogen with boron tribromide in dichloroethane or dichloromethane, hydrobromic acid or trimethylsilyliodide using appropriate conditions. For example, see also M. V. Bhatt and S. U. Kulkarmi, *Synthesis* (4), 249 (1983) for a review of the cleavage of ethers.

The intermediates of Formula III wherein $R_6$ is alkyl of from six to twenty carbons, inclusive, are known or can be readily prepared by an ordinarily skilled artisan. However, the novel intermediate of Formula III wherein $R_6$ is $-CH=CH-R_4$ and $-(CH_2)_n-R_4$ or $(CH_2)_nCOR_4$ are prepared by a synthetic sequence as shown for $III_2$, $III_3$, and $III_4$ in Schemes III or IV, respectively. More specifically, the compound of Formula $IV_1$, wherein $R_7$ are the optional substituents for the phenyl as defined above for $R_4$, a is an integer of from 0 to 5, and $R_5$ is as defined above; is prepared in a manner shown in Scheme II which is analogous to the method disclosed by P. Pfeiffer and S. Sergiewskaya, Ber., 44: 1109 (1911). Subsequent reduction of compounds of Formula $IV_1$ is accomplished by either $H_2$ and Raney nickel or iron and hydrochloric acid or dithionate to produce the compound of Formula $III_2$ or Formula $III_3$, respectively, wherein $R_7$ and $R_5$ are as defined above. The reduction is carried out in conditions within the ranges known for the reagents. Reduction of $IV_1$ by catalytic hydrogenation using a Raney nickel catalyst within the range of conditions known for this reduction produces compounds of Formula $III_2$ reducing both the nitro-moiety and unsaturation of the hydrocarbon chain in $-CH=CH-R_4$ of the $R_6$ definition with the compound of Formula I above. Reduction of $IV_1$ with iron and HCl or dithionate selectively reduces the nitro moiety.

Intermediate compounds of Formula $III_4$ wherein $R_5$ and $R_7$ are as defined above are obtained by catalytic addition of $H_2$ to the compound of Formula $IV_2$ over a palladium/carbon catalyst using conditions within those known or without unreasonable experimentation for hydrogenation using $H_2$ with these catalysts. Scheme IV shows the hydrogenation of the intermediate precursor having Formula $IV_2$ to obtain $III_4$. The compounds of Formula $IV_2$ having $R_5$ and $R_7$ as defined above are prepared in a manner analogous to known Friedel-Crafts acylation methods as disclosed by Tadkod, et al, *J. Karnatack Univ.*, 3: 78–80 (1958). The Scheme IV also shows preparation of the compounds of Formula $IV_2$.

The intermediates of Formula II wherein Q, y, and R are as defined above are synthesized by a process relative to the definitions of Q shown from (a) through (g) above.

For example, generally, the compounds of Formula II wherein Q is $I_1$ as defined above are prepared by a process shown in Scheme V. The starting material of Formula $XLII_1$, wherein $R_1$ is as defined above, is prepared in a process analogous to the method described by L. H. Helberg and A. Juarez, in *Tetrahedron Letters*, 40: 3553 (1974). The treatment of the material of Formula $XLII_1$ wherein $R_1$ is as defined above, by dropwise addition of oxalyl chloride to the material in an organic solvent such as diethyl ether, results in the compound of Formula $XXXII_1$ wherein $R_1$ is defined above. The addition is made over a period of about 50 minutes at room temperature under nitrogen. The mixture is stirred further for from 15 hours to 24 hours. Controlled oxidation of the compound of Formula $XXXII_1$ with, for example, m-chloroperbenzoic acid produces compounds of Formula $XXII_1$ wherein $R_1$ is as defined above and a is one. However, the use of excess oxidizing agent, even in the case of m-chloroperbenzoic acid, produces the compound of Formula $XXII_1$ where $R_1$ is as defined above but a is equal to two. Such oxidation proceeds under nitrogen in an inert organic solvent such as dichloromethane at a temperature of about 0° C. to $-10°$ C. preferably about 5° C. The reaction is controlled by the dropwise addition of the oxidation agent.

The compound of Formula $XXXII_1$, $XXII_1$, or $II_1$ is subsequently reacted as shown for the compound of Formula II in Scheme I, that is, in the form of the ketolactone or as the ester thereof having the Formula $XXXII_1/XXII_1/II_1$ wherein $R_1$, a, and R is as defined above. The esters of Formula $II_1$ are prepared by the methods analogous to those detailed by I. W. S. Still and M. T. Thomas, *J. Org. Chem.*, 33: 2730 (1968).

The intermediates of Formula II wherein Q is $I_2$ as defined above are disclosed in various references as discussed above or can be readily prepared in a manner analogous to known procedures.

Likewise, intermediates of Formula II wherein $R_1$ is as defined above, Q is $I_3$ wherein R is lower alkyl is known in the literature or can be readily prepared from known processes. Similarly, a compound of Formula $XII_3$ wherein $R_1$ is as defined above are known. See P. O. Corcoran, et al, *J. Org. Chem.*, 27, p. 586 (1962) and F. Dallacker and W. Korb, Ann., 694, 98 (1966). Reactions of a compound of Formula $XII_3$ to prepare a compound of Formula I wherein Q is $I_3$ is shown in Scheme VI. The conditions of the reactions shown in Scheme VI may be analogous to those described in Wiseman, et al, *J. Med. Chem.*, 16, p. 131 (1973). The reactant of the Formulae XIII and XXIII may be prepared from the Compound III by methods analogous to those known for the preparation of amides.

The intermediates of Formula II wherein $R_4$ is as defined above and Q is $I_4$ are known can be prepared by known methods when y is one or two prepared in a manner analogous to the procedure disclosed by B. Lamm and C. J. Aurell, in Acta Chemica Scand., Ser. B., p. 435 (1982) or by adding a suspension of 5-chloro-3-hydroxybenzo[b]thiophene or appropriately substituted variation in an organic solvent such as ether to a mixture prepared by adding a lower dialkyl ester or oxalic acid to a suspension of sodium methoxide in anhydrous ether all under nitrogen. Generally, the temperatures of the suspensions and mixture thereof is maintained at from about $-10°$ to about 15° C. during the mixing and subsequently stirred at room temperature for about an hour. The 5-chloro-3-hydroxybenzo[b]thiophene or appropriately substituted variation refers to a compound wherein $R_1$ is present and is as defined above. Such a thiophene is either known or prepared by known methods. See L. H. Werner, et al, *J.A.C.S.*, 79, 1679 (1957) and M. S. ElShanta et al, *J. Chem. Soc.* (C) 2364 (1967).

The intermediates of Formula II wherein R is as defined above and Q is $I_5$ are known or can be prepared by known methods when y is one. However, these intermediates when y is two are novel and are prepared as shown in Scheme VII. R is in a ketolactone form in Scheme VII. The preparation of the compound of Formula $XXII_5$ wherein $R_1$ is as defined above is analogous to that described by L. H. Helberg and A. Zuarez. *Tetrahedron Letters*, 40, 3553 (1974). Oxalyl chloride is added dropwise over a period of about one-half to one hour to a suspension of the compound of Formula $XXII_5$ in an anhydrous organic solvent such as ether. The temperature of the suspension during addition is about room temperature.

The preparation of the intermediate of Formula II wherein R is as defined above and Q is $I_6$ is described in copending U.S. patent application Ser. No. 456,121 now issued as U.S. Pat. No. 4,503,236 (1985). Such intermediates can be used as described above in Scheme I or can be further decarboxylated to form a compound of Formula $XII_6$ (see Scheme VIII) wherein $R_1$ and $R_2$ are as defined above. The decarboxylation is analogous to that discussed above in preparing an intermediate of Formula $XII_3$. The compound of Formula $XII_6$ is subsequently reacted as shown in Scheme VIII with a compound of Formula XIII or of Formula XXIII previously described and shown as reactants in Scheme VI. Again see E. H. Wiseman, et al, *J. Med. Chem.*, 16, 131 (1973).

Finally, the intermediates of Formula II wherein R is as defined above and Q is $I_7$ when y is one are known or readily prepared from known processes. See the disclosure by P. Friedlander and K. Kunz, *Chem. Ber.*, 55, 1597 (1922) and A. Etiene, *Bull. Soc. Chim. Fr.*, 15, 651 (1948) to compounds of Formula II having Q equal to $I_7$ wherein $R_3$ is hydrogen. Protection of the enolic OH is readily accomplished by known protecting groups so the reactions of Scheme I as discussed above can proceed. The compounds of Formula II having Q as $I_7$ wherein y is two are also generally known or can be made by known processes. See, for example, N. Bühler, et al, U.S. Pat. No. 4,260,544 (1981).

Compounds wherein X is lower alkyl can be prepared by an appropriate process step analogous to known processes.

Under certain circumstances it is necessary to protect either the N or O of intermediates in the above noted process with suitable protecting groups which are known. Introduction and removal of such suitable oxygen and nitrogen protecting groups are well known in the art of organic chemistry; see for example "Protective Groups in Organic Chemistry," J. F. W. McOmie, ed., (New York, 1973), pages 43ff, 95ff; J. F. W. McOmie, *Advances in Organic Chemistry*, Vol. 3, 191–281 (1963); R. A. Borssonas, *Advances in Organic Chemistry*, Vol. 3, 159–190 (1963); and J. F. W. McOmie, *Chem. & Ind.*, 603 (1979).

Examples of suitable oxygen protecting groups are benzyl, t-butyldimethylsilyl, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

The salts of compounds of Formula I described above are prepared by reacting the appropriate base or acid with a stoichometric equivalent of the acid enol or N base compounds of Formula I, respectively, to obtain pharmacologically acceptable salts thereof.

DETAILED DESCRIPTION OF THE INVENTION

By the term, "alkyl of from 6 to 20 carbons, inclusive" is meant any branched or unbranched saturated hydrocarbon grouping having the noted number or carbons, such as hexyl, heptyl, octyl, nonyl, decyl, dodecyl, and the like, and isomers thereof.

The term "alkoxy of from one to four carbons, inclusive" means methoxy, ethoxy, propoxy, or butoxy, and isomers thereof attached to the parent molecular residue through an oxygen atom. Thioalkoxy of from one to four carbons, inclusive, is the same except attached through a sulfur atom.

The term "monoalkyl- or dialkyl-amino having of from one to four carbons, inclusive," means respectively, one or two alkyl groups, as previously defined for of from one to four carbons, inclusive, attached to the parent molecular residue through a nitrogen atom.

The term "alkanoyl of from one to four carbons, inclusive," means a branched or unbranched alkyl, as previously defined for of from one to four carbons, inclusive, attached to the parent molecule residue through the carbonyl group.

The term "hydroxyalkyl of from one to four carbons, inclusive," is an hydroxy attached through an alkyl group, as previously defined for of from one to four carbons, to the parent molecular residue.

The term "alkanoylamino of from two to six carbons, inclusive," means an alkanoyl, as previously defined by including also pentyl or hexyl and isomers thereof among the alkyl attached to the parent molecule residue through the amino group.

The term "carboxyalkoxy having alkoxy of from one to four carbons, inclusive," means an alkyl, as previously defined for alkyl of from one to four carbons, inclusive, attached to the oxygen atom of an ester group, through which the alkyl is attached to the parent molecular residue.

The term "alkanesulfonamide of from one to four carbons, inclusive," means an alkyl, as defined above for of from one to four carbons, attached to the nitrogen atom or a sulfonamide moiety and thus through the sulfur atom to the parent molecular residue.

"Halogen" means fluorine, chlorine, bromine, iodine, or trifluoromethyl.

"Carboalkoxyamide of from one to four carbons, inclusive," means an alkyl, as defined above for of from one to four carbons, inclusive, attached to the oxygen atom of an ester group which carboxyl is in turn attached to the parent molecule residue through an amino group.

"Alkyl sulfinyl" and "alkyl sulfonyl" are respectively, an alkyl attached to the parent residue molecule through a sulfinyl and sulfonyl group.

DESCRIPTION OF THE PREFERRED EMBODIMENTS

The invention is further elaborated by the representative examples as follows. Such examples are not meant to be limiting thereto.

I. Preparation of compounds of Formula IV

A. For compounds of Formula IV, see Scheme II.

PREPARATION A 1,2-Dimethoxy-4-[2-(4-nitrophenyl)ethenyl]benzene (See Scheme II, Formula IV$_1$, wherein c is two, R$_7$ is methoxy, R$_5$ is hydrogen)

A mixture of 272 g (1.5 mole) of p-nitrophenylacetic cid and 249 g (1.5 mole) of 3,4-dimethoxybenzaldehyde in a 2.0 l nitrogen-filled flask was heated to 60° C. (temperature of reaction mixture) on the steam bath. Piperidine (150 ml; 129 g, 1.52 mole) was added to the warm reaction mixture in small portions over 15 minutes. After ~50 ml of piperidine had been added, a mild exotherm developed, and the temperature of the reaction mixture rose to 95° C. without external heating. The steam bath was replaced by a heating mantle, and the mixture was heated to reflux over 15 minutes, then maintained at 110°–120° C. for four hours. The reaction mixture was cooled to 70° C. and stirred vigorously while 500 ml of methanol was added. After cooling the mixture in ice, the precipitate that formed was filtered, stirred in 1.0 l of fresh methanol, and refiltered. There was obtained 219 g (51% yield) of olefin product, mp 132°–134° C.

PREPARATION B 1,2-Dichloro-4-[2-(4-nitrophenyl)ethenyl]benzene (See Scheme II, Formula IV$_1$ wherein c is two, R$_7$ is chloro, and R$_5$ is hydrogen)

Prepared by the procedure described in Preparation A, from p-nitrophenylacetic acid (125 g, 0.69 mole) and 3,4-dichlorobenzaldehyde (121 g, 0.69 mole). There was obtained 70 g (35% yield) of the product, mp 197°–199° C.

In an analogous manner to that found in above Preparation A starting materials the following compounds of Formula IV$_1$ are prepared (see Scheme II).

PREPARATION C

4-[2-[(4-Nitrophenyl)ethenyl][1,1-biphenol] mp 238°–239° C.

PREPARATION D

1-Methoxy-4-[2-(4-nitrophenyl)ethenyl]-2-(phenylmethoxy)benzene, mp 139°–144° C.

PREPARATION E 1,2-Dimethyl-4-[2-(4-nitrophenyl)ethenyl]benzene, mp 113°–115° C.

PREPARATION F 1,3-Dimethoxy-5-[2-(4-nitrophenyl)ethenyl]benzene, mp 145°–146° C.

PREPARATION G

2-[2-(4-Nitrophenyl)ethenyl]naphthalene, mp 168°–170° C.

PREPARATION H 1,2,3-Trimethoxy-5-[2-(4-nitrophenyl)ethenyl]benzene, mp 192°–195° C.

PREPARATION I 1,2-Dimethoxy-3-[2-(4-nitrophenyl)ethenyl]benzene, mp 143°–145° C.

PREPARATION J 2,4-Dimethoxy-1-[2-(4-nitrophenyl)ethenyl]benzene, mp 107°–110° C.

PREPARATION K 1,2-Dimethoxy-4-[2-(2-nitrophenyl)ethenyl]benzene, mp 134°–137° C.

B. For compounds of Formula IV$_2$ see Scheme IV

PREPARATION L

N-[2-Methoxy-5-[(4-nitrophenyl)acetyl]phenyl]acetamide (See Scheme IV, Formula IV$_2$ Wherein c is two, R$_7$ is methoxy and Acetamide, n is one, and R$_5$ is hydrogen)

A mixture of anhydrous AlCl$_3$ (36 g, 270 mmol) and 50 ml of CH$_2$Cl$_2$ is cooled to 0° in an ice bath. 2-Acetylanisidine (33 g, 200 mmol) is added to the stirring mixture. A solution of 39.9 g (200 mmol) of 4-nitrophenylacetyl chloride in 130 ml of CH$_2$Cl$_2$ is added slowly to the cooled reaction mixture. The reaction mixture is stirred at 0° C. for 0.75 hour and 22 hours at room temperature. The reaction mixture is poured onto a mixture of 800 ml ice and 40 ml concentrated hydrochloric acid and allowed to stir for 1.25 hours before extraction with CH$_2$Cl$_2$. The CH$_2$Cl$_2$ extract is evaporaed to a dark oily residue which crystallized from MeOH to give 28 g (52%) of a yellow solid. Further recrystalliztion from MeOH gave the pure product, mp 200°–203° C.

In a manner analogous to that found above in Preparation L using appropriate starting materials the following compounds of Formula IV$_2$ are prepared.

PREPARATION M 1-(3,4-Dimethoxyphenyl)-3-(4-nitrophenyl)propanone, mp-126°–132° C.

PREPARATION N 1-(3,4-Dimethoxyphenyl)-4-(4-nitrophenyl)butanone, mp 109°–112° C.

II. Preparation of Compounds of Formula III

A. For compounds of Formula III$_2$ and III$_3$ see Scheme III.

PREPARATION 1

4-[2-(3,4-Dimethoxyphenyl)ethyl]benzeneamine (See Scheme III Formula III$_2$ Wherein c is 2, R$_7$ is 3,4-dimethoxy, and R$_5$ is Hydrogen A mixture of 19.4 g (0.068 mole) of 1,2-dimethoxy-4-[2-(4-nitrophenyl)etheno]benzene as prepared in Preparation A above, and 0.20 g 10% Pd/C catalyst in 200 ml of N,N-dimethylformamide was hydrogenated at 55 psig H$_2$ pressure for 16 hours. The catalyst was removed by filtration, and the filtrate was evaporated. Recrystallization of the residue from methanol yielded 12.3 g (70% yield) of the amine product, mp 116°–117° C.

PREPARATION 2

4-[2-(3,4-Dichlorophenyl)ethyl]benzenamine (See Scheme III, Formula III$_2$ Wherein R$_7$ is 3,4-dichloro, c is two, and R$_5$ is Hydrogen)

A mixture of 62.3 g (0.21 mole) of 1,2-dichloro-4-[2-(4-nitrophenyl)etheno]benzene as prepared in Preparation B above, and 2.0 g of Raney Nickel catalyst in 935 ml of tetrahydrofuran was hydrogenated at 65 psig H$_2$ pressure for 20 hours. The catalyst was removed by filtration, and the filtrate was evaporated. Recrystallization of the residue from hexane/dichloromethane yield 49 g (87% yield) of the amine product, mp 73°–75° C.

In a manner analgous to that found above in Preparations 1 and 2 using appropriate starting materials, as prepared in Preparations C through F corresponding to the following Preparations 3 through 6 and thereafter as indicated for Preparations 8 through 18. The following compounds of Formula III$_2$ are prepared.

PREPARATION 3

4-[2-(1,1'-Biphenyl)-4-ylethyl]benzenamine, mp 109°–111° C.

PREPARATION 4

4-[2-(2-Naphthylenyl)ethyl]benzeneamine, mp 123°–125° C.

PREPARATION 5

4-[2-(3-Hydroxy-4-methoxyphenyl]benzenamine, mp 152°–154° C.

PREPARATION 6

4-[2-(3-Methoxyphenyl)ethyl]benzenamine, mp 49°–51° C.

PREPARATION 7

4-[2-(3,4-Dihydroxyphenyl)ethyl]benzenamine as an acetate salt, mp 216°–218° C.

A mixture of 20 g (78 mmol) of 4-[2-[3,4-dimethoxyphenyl)ethyl]aniline which is prepared in Preparation 1 above and 300 ml of of 48% hydrobromic acid is stirred at reflux under nitrogen for seven hours and at room temperature overnight. The resultant precipitate is collected, washed with ether, and redissolved in 1N.NaOH. The solution is acidified to pH 6 with glacial HOAc and the resultant precipitate is collected as crude product. Recrystallization from H$_2$O and then from MeOH yields the 4-[2-(3,4-dihydroxyphenyl)ethyl]benzenamine as an acetate salt; yield, 13.4 g (76%), mp 216°–218° C.

PREPARATION 7A 1,2-Benzenediol, 4-[2-(4-aminophenyl)ethyl]diacetate

4-[2-(3,4-Dihydroxyphenyl)ethyl]benzenamine hydrobromide as prepared in Preparation 7 above (53.3 g, 0.17 mole) is added to a stirred solution of acetylbromide (67.6 g, 0.549 mole) and trifluoroacetic acid (670 ml). The mixture is stirred at room temperature for 3.5 hours. The excess of acetyl bromide and trifluoroacetic acid is then removed at <25° C. under reduced pressure. The residue after trituration with ether (~1 l) gave 63.47 g of a white solid, mp 165° C. (dec). This hydrobromide salt is suspended in ~1 l of ice-water and ~1.5 l of ether and carefully made basic with 1N sodium bicarbonate solution while the temperature is maintained below 10° C. The ether layer is separated and the aqueous layer is extracted with ether. The combined ether extract is dried and evaporated to give 46 g (85.3%) of a pure product, mp 100°–1° C. Recrystallization from methylene chloride-methanol gives 24.9 g (46.3%) of analytically pure product, mp 100°–1° C.

PREPARATION 8

4-[2-(2,3-Dimethoxyphenyl)ethyl]benzenamine.HCl, mp 135°–136° C.

The starting material, 1,2-dimethoxy-3-[2-(4-nitrophenyl)ethenyl]benzene, is as prepared in Preparation I above.

PREPARATION 9

4-[2-(2,4-Dimethoxyphenyl)ethyl]benzenamine, mp 56°–58° C.

The starting material, 2,4-dimethoxy-1-[2-(4-nitrophenyl)ethenyl]benzene, is as prepared in Preparation J above.

PREPARATION 10

4-[2-(3,4,5-Trimethoxyphenyl)ethyl]benzenamine, mp 91°–93° C.

The starting material, 1,2,3-trimethoxy-5-[2-(4-nitrophenyl)ethenyl]benzene, is as prepared in Preparation H above.

PREPARATION 11

4-[2-(3,5-dimethoxyphenyl)ethyl]benzenamine.HCl, mp 155°–157° C.

The starting material, 1,3-dimethoxy-4-[2-(4-nitrophenyl)ethenyl]benzene, is prepared in a manner analogous to Preparations A through K.

PREPARATION 12

4-[2-(2-Chlorophenyl)ethyl]benzenamine.HCl, mp 208°–211° C.

The starting material, 2-chloro-1-[2-(4-nitrophenyl)ethenyl]benzene, is prepared in a manner analogous to Preparations A through K.

PREPARATION 13

4-[2-(2-Methylphenyl)ethyl]benzenamine.HCl, mp 171°–173° C.

The starting material, 2-methyl-1-[2-(4-nitrophenyl)ethenyl]benezene, is prepared in a manner analogous to Preparation A through K.

PREPARATION 14

4-[2-(4-Butoxyphenyl)ethyl]ethylbenzenamine, mp 58°–59° C.

The starting material, 4-butoxy-1-[2-(4-nitrophenyl)ethenyl]benzene, is prepared in a manner analogous to Preparations A through K.

PREPARATION 15

2-[2-(3,4-Dimethoxyphenyl)ethyl]benzenamine, mp 58°–60° C.

The starting material, 1,2-dimethoxy-4-[2-(2-nitrophenyl)ethenyl]benzene, is as prepared in Preparation K above.

PREPARATION 16

N-[2-methoxy-5-[(4-aminophenyl)ethyl]phenyl]acetamide, mp 135°–140° C.

The starting material, N-[2-methoxy-5-[(4-nitrophenyl)ethyl]phenyl]acetamide, is prepared in a manner analogous to the methods of Preparations A through K.

PREPARATION 17

4-[3-(3,4-dimethoxyphenyl)propyl]benzamine, mp 54°–57° C.

The starting material, 1,2-dimethoxy-4-[2-(2-nitrophenyl)propenyl]benzene, is prepared in a manner analogous to Preparations A through K above.

PREPARATION 18

4-[4-(3,4-Dimethoxyphenyl)butyl]benzamide, mp 97°–100° C.

The starting material, 1,2-dimethoxy-[2-(2-nitrophenyl)butenyl]benzene is prepared in a manner analogous to Preparations A through K above.

B. An alternate method of preparation for a compound of Formula III wherein R$_6$ is (CH$_2$)$_n$-R$_4$ wherein n is 1 or 2 is as follows

PREPARATION 19

4-[(3,4-Dimethoxyphenyl)methyl]aniline (see Scheme III, Formula III$_2$ Wherein c is two, R$_7$ is Methoxy and R$_5$ is Hydrogen)

Mixture of glacial acetic acid (100 ml), 20% Pd/C catalyst (0.5 g) and 3,4-dimethoxy-4'-nitrobenzophenone (Tadkod, Kulkarni, and Nargund, *J. Karnatak Univ.*, 3, 78–80 (1958)) (5.4 g, 18.8 mmol) is hydrogenated at 52 psi for about five hours.

Concentrated H$_2$SO$_4$ (1.1 ml) and additional 20% Pd/C (0.5 g) are added and the hydrogenation is continued until five equivalents are consumed (21.2 hours). Potassium acetate (2 g, 20 mmol) is added to the mixture and the catalyst is removed by filtration through celite. The filtrate is acidified with concentrated HCl (1.7 ml), concentrated in vacuo to a residual oil and dissolved in 10% HCl (400 ml). The acidic solution is washed with Et$_2$O (2×400 ml) and CH$_2$Cl$_2$ (1×100 ml) and then basified with Na$_2$CO$_3$. The aqueous fraction was extracted with $CH_2Cl_2$ and the $CH_2Cl_2$ extract was dried with $Na_2SO_4$. Evaporation of the volatile solvent in vacuo gave 4.4 g (96%) of crude oily product which crystallized upon standing. The analytical amine was obtained by column chromatography; yield, 1.58 g (35%), mp 101°–104°.

An intermediate 4-(3,4-trimethylsilyloxyphenethyl)aniline is prepared in the following example for use in preparing the compound of Formula II wherein Q is $L_4$.

PREPARATION 20

4-(3,4-Trimethylsilyloxyphenethyl)aniline

A mixture of 4-(3,4-dihydroxyphenethyl)aniline (34.39 g, 0.15 mole) and hexamethyldisilazane (24.2 g, 0.15 mole) is heated in a wax bath at 120°–160° C. for 3.75 hours under nitrogen, to give dark colored oily residue, which is chromatographed on silica gel (160 g). Elution with chloroform gives oily product (47.1 g, 84%) of satisfactory purity for the next step.

III. Preparation of Compounds of Formula II

PREPARATION I

4H-[1]-Benzothiopyrano[4,3-b]furan-2,3-dione (See Scheme V, Formula $XXXII_1$ Wherein $R_1$ is hydrogen)

To a stirred mixture of 4-[trimethyl[silyl]oxy]-2H-benzothiopyran (380.5 g, 1.609 mol), prepared according to the method of L. Hellberg et al, *Tet. Letters*, 3553–3554 (1974), and one liter of diethyl ether, were added 103.8 g (0.818 mol) of oxalyl chloride in a dropwise manner over a period of 50 minutes at room temperature under nitrogen. The mixture was stirred at room temperature for 17 hours after which time the ether was removed under reduced pressure. The residue was triturated with isopropyl ether/hexane to give 146.9 g (82.3%) of a brown crystalline solid, mp 156° C. (dec).

PREPARATION II

4H-[1]Benzothiopyrano[4,3-b]furan-2,3-dione-S-oxide (See Scheme V Formula $XXII_1$ Wherein $R_1$ is Hydrogen and a=1)

A stirred mixture of 4H-[1]benzothiopyrano[4,3-b]furan-2,3-dione (30.48 g, 0.139 mol) in 500 ml of dichloromethane was cooled under nitrogen to a temperature between −6° C. and −2° C. A solution of m-chloroperbenzoic acid (24.1 g, 0.139 mol) in 500 ml of dichloromethane was added dropwise over a period of about 70 minutes. After the addition was complete, the mixture was stirred overnight at room temperature. The product, 4H-[1]benzothiopyrano-[4,3-b]furan-2,3-dione-S-oxide, was collected by filtration and washed with isopropyl ether to give 13 g, of material, mp 165° C., (dec).

PREPARATION III

4H-[1]Benzothiopyrano(4,3-b]furan-2,3-dione, S,S-dioxide (See Scheme V, Formula $XXII_1$ Wherein $R_1$ is Hydrogen and a=2)

A stirred mixture of 4H-[1]benzothiopyrano[4,3-b]furan-2,3-dione (26.2, 0.12 mol) and 500 ml of dichloromethane was cooled under nitrogen to a temperature between −8° C. and −6° C. A solution of m-chloroperbenzoic acid (48 g, 0.728 mol) in 500 ml of dichloromethane was added dropwise over a period of about 17 minutes. After the addition was complete, the mixture was stirred at this temperature for 30 minutes and then at room temperature for 19 hours.

The solid which formed was removed by filtration and washed with dichloromethane to yield 28.4 g of m-chlorobenzoic acid. The filtrate was concentrated under reduced pressure and the residual solid was recrystallized twice from tetrahydrofuran-isopropyl ether to yield 16.1 g (53.6%) of 4H-[1]benzothiopyrano[4,3-b]furan-2,3-dione, S,S-dioxide, as a light yellow crystalline solid, mp 174°–176° C.

PREPARATION IV

Benzo[b]thiophene-2-acetic acid; 5-chloro-3-hydroxy-α-oxo-methyl ester (See Scheme I, Formula II, Where Q is $L_4$ wherein $R_1$ is 5-chloro; y is two; R is methyl)

To a stirred suspension of sodium methoxide (22.34 g, 0.41 mole) in anhydrous ether (1.6 l) under nitrogen at room temperature is added dimethyl oxalate (48.9 g, 0.41 mole). After 20 minutes the mixture is cooled to 10° C. and a suspension of 5-chloro-3-hydroxybenzo[b]thiophene (L. H. Werner, et al, JACS, 79, 1679 (1957); M. S. ElShanta, et al, *J. Chem. Soc.*, (C)2364 (1967)) (76.4 g, 0.41 mole) in ether (1.45 l) is added over a period of 30 minutes. After the addition the mixture is stirred at ~10° C. for three hours and then at room temperature for one hour. After cooling to ~10° C., cold 4% aqueous sulfuric acid (1 l) is added and stirred for one hour.

The precipitate is filtered off, washed with water and with ether to give 62.6 g of a solid, mp 185°–6° C. Recrystallization from methylene chloride gives 54.5 g (49.1%) of a light-brown crystalline solid, mp 185°–6° C. An additional 4.1 g (3.7%) of product, mp 185°–6° C., is obtained from ether.

Starting materials of Formula $XII_6$ as shown in Scheme VIII may be prepared as exemplified in the following Preparations V or VI.

PREPARATION V

4-Methyl-2H-furo[3,2-b]indole-3(4H)-one (See Scheme VIII, Formula $XII_6$ Wherein $R_1$ is hydrogen and $R_2$ is methyl)

A mixture of 47.0 g (0.18 mole) of 3-hydroxy-4-methyl-4H-furo[3,2-b]indole-2-carboxylic ethyl eser (Prep. described in U.S. patent application Ser. No. 369,448) in 450 ml of 95% ethanol was treated with 450 ml of 30% aqueous sodium hydroxide. The mixture was stirred at reflux for two hours, cooled, added to 3.0 kg ice/water, and acidified with 6.0N hydrochloric acid. The product was filtered, washed with water, and recrystallized from ethanol-water to yield 17.9 g (53% yield) of the product, mp 113°–116° C. An additional recrystallization as above raised the mp to 115.5°–118° C.

PREPARATION VI

7-Methoxy-4-phenyl-2H-furo[3,2-b]indole-3(4H)-one (See Scheme VIII, Formula $XII_6$ Wherein $R_1$ is methoxy, and $R_2$ is phenyl)

A mixture of 39.0 g (0.12 mole) of 3-hydroxy-7-methoxy-4-phenyl-4H-furo[3,2-b]indole-2-carboxylic methyl ester (Preparation described in U.S. patent application Ser. No. 369,448 now issued as U.S. Pat. No. 4,503,236) in 195 ml of N,N-dimethylformamide and 80 ml of water was treated with 40 ml of 50% aqueous sodium hydroxide, After heating on the steam bath for two hours, the product was isolated as described in Example V above. Recrystallization from 2-methoxyethanol/N,N-dimethylformamide yielded 15.8 g (49% yield) of the product, mp 175° C.-dec. An additional recrystallization as above raised the mp to 185°–187° C.

IV. Preparation of Compounds of Formula I Wherein Q is I₁

EXAMPLE 1

N-[4-[2-(3,4-Dihydroxyphenyl)ethyl]phenyl]-4-hydroxy-α-oxo-2H-1-benzothiopyran-3-acetamide (See Scheme I, Formula I Wherein Q is I₁ Wherein a is zero, and b is zero, y is 2, R₅ is hydrogen, and R₆ is 2-(3,4-dihydroxyphenyl)ethyl A mixture of 4H-[1]benzothiopyrano[4,3-b]furan-2,3-dione, as prepared in Preparation I above (18.6 g, 0.085 mol) and 4-[2-(3,4-dihydroxyphenyl)ethyl]benzenamine as prepared in Preparation 7 above (17.1 g, 0.0749 mol) in 500 ml of dry tetrahydrofuran was stirred under nitrogen at room temperature for 18 hours in the dark. The solvent was removed under pressure, and the resulting solid was stirred in 800 ml of dichloromethane under reflux for one and one-half hours and then cooled to room temperature.

The resulting precipitate was removed by filtration and washed with dichloromethane to yield 27.8 g of a light yellow solid, mp 165°–166° C. A further crop of 4.9 g of crystals, mp 165°–166° C., was obtained from the mother liquor. The two crops were combined and recrystallized from acetonitrile to yield 28.6 g (85.2%) of N-[4-[2-(3,4-dihydroxyphenyl)ethyl]phenyl]-4-hydroxy-α-oxo-2H-1-benzothiopyran-3-acetamide, mp 166°–167° C.

EXAMPLE 2

N-[4-[2-(3,4-Dihydroxyphenyl)ethyl]phenyl]-4-hydroxy-α-oxo-2H-1-benzothiopyran-3-acetamide, 1-oxide (See Scheme I, Formula I Wherein Q is I₁, Wherein a is one, and b is zero; y is two; R₅ is hydrogen; and R₆ is 2-(3,4-dihydroxyphenyl)ethyl)

A stirred mixture of N-[4-[2-(3,4-dihydroxyphenyl)ethyl]phenyl]-4-hydroxy-α-oxo-2H-1-benzothiopyran-3-acetamide as prepared in Example 1 above (17 g, 0.038 mol) in 2.5 liters of dichloromethane was cooled under nitrogen to a temperature of about −10° C. To this mixture was added dropwise over a period of about 50 minutes, a solution of 13.1 g (0.076 mol) of m-chloroperbenzoic acid in 500 ml of chloroform. The resulting mixture was stirred at room temperature overnight.

The precipitate which formed was removed by filtration, washed with chloroform, and recrystallized from tetrahydrofuran-ethyl acetate to yield 15 g (82.4%) of N-[2-[(3,4-dihydroxyphenyl)ethyl]phenyl]-4-hydroxy-α-oxo-2H-1-benzothiopyran-3-acetamide, 1-oxide as a light yellow crystalline solid, mp 185° C. (dec).

EXAMPLE 3

N-[4-[2-(3,4-Dimethoxyphenyl)ethyl)phenyl]-4-hydroxy-α-oxo-2H-1-benzothiopyran-3-acetamide, 1,1-dioxide (See Scheme I, Formula I Wherein Q is I₁, Wherein a is two, and b is zero; y is two, R₅ is hydrogen; and R₆ is 2-(3,4-dimethoxyphenyl)ethyl A stirred mixture of N-[4-[2-(3,4-dimethoxyphenyl)ethyl]phenyl]-4-hydroxy-α-oxo-2H-1-benzothiopyran-3-acetamide as prepared in Example 1 above (18 g, 0.0393 mol) and 600 ml of dichloromethane was cooled to a temperature of about −8° C. under nitrogen. To this cooled mixture were added 13.7 g (0.079 mol) of m-chloroperbenzoic acid in 400 ml of dichloromethane over a period of about 25 minutes.

The stirred mixture was allowd to slowly warm to room temperature and stirred for an additional 19 hours. The solution was then washed successively with two 1-liter portions of saturated sodium bicarbonate solution and then a one-liter portion of water. The organic phase was separated, dried, and evaporated to yield 18.3 g of a yellow solid, mp 180°–181° C.

Recrystallization from tetrahydrofuran-ethanol yielded 14.5 g (72.6%) of N-[4-[2-(3,4-dimethoxyphenyl)ethyl]phenyl]-4-hydroxy-α-oxo-2H-1-benzothiopyran3-acetamide, 1,1-dioxide as light organge crystals, mp 184°–185° C.

In a manner analogous to appropriate Examples 1, 2, or 3 above and using respective starting materials the following compounds of Formula I wherein Q is I₁ and a is zero, one, or two, and y is two are prepared.

EXAMPLE 4

N-[4-[2-(4-chlorophenyl)ethyl]phenyl]-4-hydroxy-α-oxo-2H-1-benzothiopyran-3-acetamide, mp 144°–145° C.

EXAMPLE 5

N-[4-[2-(3,4-Dimethoxyphenyl)ethyl]phenyl]-4-hydroxy-α-oxo-2H-1-benzothiopyran-3-acetamide, mp 146°–148° C.

EXAMPLE 6

N-[4-[2-(3,4-Dihydroxyphenyl)ethyl]phenyl]-4-hydroxy-α-oxo-2H-1-benzothiopyran-3-acetamide, 1,1-dioxide, mp 190° C. (dec)

EXAMPLE 7

N-[4-[2-(3,4-Dichlorophenyl)ethyl]phenyl]-4-hydroxy-α-oxo-2H-1-benzothiopyran-3-acetamide, mp 172°–173° C.

EXAMPLE 8

N-[2-[2-(3,4-Dichlorophenyl)ethyl]phenyl]-4-hydroxy-2H-1-benzothiopyran-3-carboxamide, 1,1-dioxide, mp 180°-2° C.

EXAMPLE 9

N-(4-Decylphenyl)-4-hydroxy-α-oxo-2H-1-benzothiopyran-3-acetamide, 1,1-dioxide, mp 114°–116° C.

EXAMPLE 10

N-(4-Decylphenyl)-4-hydroxy-α-oxo-2H-1-benzothiopyran-3-acetamide, mp 89°–90° C.

Using appropriate starting materials, esters of the Formula II₁ as shown in Scheme V are prepared in a manner analogous to that discussed above citing I. W. J. Still and M. T. Thomas. Then the esters are used as shown in Scheme I by Formula II, wherein Q is I₁; a is zero, one, or two; y is one or two, R₁ is as defined above, and R is lower alkyl to prepare the compound of Formula I wherein Q is I₁; a is zero, one, or two, y is one or two; R₁, R₅, and R₆ are as defined above depicted by Scheme I and exemplified as follows.

EXAMPLE 11

N-[4-[2-(3,4-Dichlorophenyl)ethyl]phenyl]-3,4-dihydro-4-oxo-2H-1-benzothiopyran-3-carboxamide, 1,1-dioxide (See Scheme I, Formula I wherein Q is $I_1$, b is zero, a is two, y is one, $R_5$ hydrogen, $R_6$ is (2-(3,4-dichlorophenyl)ethyl)

A mixture of 5.08 g (20 mmol) of methyl-3,4-dihydro-4-oxo-2H-1-benzothiopyran-3-carboxylate (prepared according to the procedure of I. W. J. Still and M. T. Thomas, *J. Org. Chem.*, 33: 2730 (1968)) and 5.32 g (20 mmol) of 4-[2-(3,4-dichlorophenyl)ethyl]benzenamine (from Preparation 2 above) in 50 ml of xylene were heated at reflux for 18 hours. The yellow precipitate which formed upon cooling the reaction mixture was collected by filtration to give 6.28 g (64%) of material melting at 238°–242° C. One recrystallization from acetone gave 5.08 g (52%) of N-[4-[2-(3,4-Dichlorophenyl)ethyl]phenyl]-3,4-dihydro-4-oxo-2H-1-benzothiopyran-3-carboxamide, 1,1-dioxide, mp 234°–236° C.

EXAMPLE 12

4-[2-[4-[[(3,4-Dihydro-4-oxo-2H-1-benzothiopyran-3-yl)carbonyl]amino]phenyl]ethyl]benzoic acid, 1,1-dioxide (See Scheme I, Formula I wherein Q is $I_1$, $R_1$ is hydrogen, b is one, a is two, y is one, $R_5$ is hydrogen, and $R_6$ is 2-(4-carboxylphenyl)ethyl A mixture of 4-[2-[4-[[(3,4-dihydro-4-oxo-2H-1-benzothiopyran-3-yl)carbonyl]amino]phenyl]ethyl]benzoic, ethyl ester, 1,1-dioxide (2 g, 4.1 mmol, from a following Example 47) and 100 ml of 5% sodium hydroxide solution was stirred and heated under reflux for one-half hour. The solution was cooled, acidified with concentrated hydrochloric acid to pH 2, and the solid which precipitated was collected by filtration. The crude product was recrystallized from methanol to yield 0.5 g of pure 4-[2-[4-[[(3,4-Dihydro-4-oxo-2H-1-benzothiopyran-3-yl)carbonyl]amino]phenyl]ethyl]benzoic acid, 1,1-dioxide, mp 256259° C.

EXAMPLE 13

N-[4-[2-[3,4-Bis(acetyloxy)phenyl]ethyl]phenyl]-4-hydroxy-2H-1-benzothiopyran-3-carboxamide, 1,1-dioxide (See Scheme I, Formula I Wherein Q is $I_1$, Wherein a is two, b is zero, y is one, $R_5$ is hydrogen and $R_6$ is 2-[3,4-bis(acetyloxy)phenyl]ethyl)

A mixture of 19.6 g (43 mmol) of N-[4-[2-(3,4-dihydroxyphenyl)ethyl]phenyl]-3,4-dihydro-4-oxo-2H-1-benzothiopyran-3-carboxamide, 1,1-dioxide, 120 ml of 10% sodium hydroxide, and 423 mmol of acetic anhydride was stirred for 20 minutes at room temperature. The precipitate which formed was collected and washed successively with water, 5% sodium bicarbonate solution, and again with water, and then dried. The orange-brown material was recrystallized from acetonitrile to yield 10.4 g (45%) of N-[4-[2-[3,4-Bis(acetyloxy)phenyl]ethyl]phenyl]-4-hydroxy-2H-1-benzothiopyran-3-carboxamide, 1,1-dioxide, mp 214°–215° C.

EXAMPLE 14

N-[4-[(3,4-Dihydroxyphenyl)methyl]phenyl]-3,4-dihydro-4-oxo-2H-1-benzothiopyran-3-carboxamide, 1,1-dioxide (See Scheme I, Formula I wherein Q is $I_1$, Wherein a is two, b is zero, y is one, $R_5$ is hydrogen; $R_6$ is (3,4-dihydroxyphenyl)methyl A suspension of 1.0 g (2.1 mmol) of N-[4-[(3,4-dimethoxyphenyl)methyl]phenyl]-3,4-dihydro-4-oxo-2H-1-benzothiopyran-3-carboxamide, 1,1-dioxide and $BBr_3 \cdot S(CH_3)_2$ (4.0 g, 12.6 mmol) in 150 ml of dichloromethane was heated under reflux under nitrogen for 18 hours. The resulting yellow suspension was poured onto 600 ml of ice water, stirred for one and one-half hours and then filtered. The crude product was recrystallized from isopropanol-water to yield 544 mg (59%) of N-[4-[(3,4-dihydroxyphenyl)methyl]phenyl]-3,4-dihydro-4-oxo-2H-1-benzothiopyran-3-carboxamide, 1,1-dioxide, mp 216°–218° C.

In a manner analogous to that found in Examples 11–12 using appropriate starting materials the following compounds are also prepared.

EXAMPLE 15

3,4-Dihydro-4-oxo-N-[(4-(phenyl)methyl]phenyl]-2H-1-benzothiopyran-3-carboxamide, 1,1-dioxide, mp 193°–196° C. (Enol form of Example 24)

EXAMPLE 16

3,4-Dihydro-4-oxo-N-[(4-(2-phenyl)ethyl]-phenyl]-2H-1-benzothiopyran-3-carboxamide, 1,1-dioxide, mp 210°–212° C.

EXAMPLE 17

N-[4-[(3,4-Dimethoxyphenyl)methyl]phenyl]-3,4-dihydro-4-oxo-2H-benzothiopyran-3-carboxamide, 1,1-dioxide, mp 170°–172° C.

EXAMPLE 18

N-[4-[2-(3,4-Dimethoxyphenyl)ethyl]phenyl]-4-hydroxy-2H-1-benzothiopyran-3-carboxamide, 1,1-dioxide, mp 191°–193° C.

EXAMPLE 19

N-[4-[3-(3,4-Dimethoxyphenyl)propyl]phenyl]-3,4-dihydro-4-oxo-2H-1-benzothiopyran-3-carboxamide, 1,1-dioxide, mp 165°–166° C.

EXAMPLE 20

N-[4-[4-(3,4-Dimethoxyphenyl)butyl]phenyl]-3,4-dihydro-4-oxo-2H-1-benzothiopyran-3-carboxamide, 1,1-dioxide, mp 184°–185° C.

EXAMPLE 21

N-[4-[2-(3,4-Dihydroxyphenyl)ethyl]phenyl]-4-hydroxy-2H-1-benzothiopyran-3-carboxamide, 1,1-dioxide, mp 218 (dec) (Enol form of Example 24)

EXAMPLE 22

N-[4-[3-(3,4-Dihydroxyphenyl)propyl]phenyl]-3,4-dihydro-2H-1-benzothiopyran-3-carboxamide, 1,1-dioxide, mp 171°–173° C.

EXAMPLE 23

N-[4-[4-(3,4-Dihydroxyphenyl)butyl]phenyl]-3,4-dihydro-4-oxo-2H-1-benzothiopyran-3-carboxamide, 1,1-dioxide, mp 196°–199° C.

EXAMPLE 24

N-[4-[2-(3,4-Dihydroxyphenyl)ethyl]phenyl]-3,4-dihydro-4-oxo-2H-1-benzothiopyran-3-carboxamide, 1,1-dioxide, mp 218° C. (Keto form of Example 21)

EXAMPLE 25

N-[4-[2-(3,4-Dimethoxyphenyl)ethyl]phenyl]-4-hydroxy-6-methoxy-2H-1-benzothiopyran-3-carboxamide, 1,1-dioxide, mp 222°-223° C.

EXAMPLE 26

6-Chloro-N-[4-[2-(3,4-dimethoxyphenyl)ethyl]-phenyl]-4-hydroxy-2H-1-benzothiopyran-3-carboxamide, 1,1-dioxide, mp 210°-213° C.

EXAMPLE 27

3,4-Dihydro-N-[4-[2-(3-hydroxy-4-methoxyphenyl)ethyl]phenyl]-4-oxo-2H-1-benzothiopyran-3-carboxamide, 1,1-dioxide, mp 230°-233° C.

EXAMPLE 28

N-[4-[2-(2,3-Dimethoxyphenyl)ethyl]phenyl]-4-hydroxy-2H-1-benzothiopyran-3-carboxamide, 1,1-dioxide, mp 188°-190° C.

EXAMPLE 29

N-[4-[2-(2,3-Dihydroxyphenyl)ethyl]phenyl]-3,4-dihydro-4-oxo-2H-1-benzothiopyran-3-carboxamide, 1,1-dioxide, mp 200°-202° C.

EXAMPLE 30

N-[4-[2-(2,4-Dimethoxyphenyl)ethyl]phenyl]-4-hydroxy-2H-1-benzothiopyran-3-carboxamide, 1,1-dioxide, mp 195°-198° C.

EXAMPLE 31

N-[4-[2-(2,4-Dihydroxyphenyl)ethyl]phenyl]-4-hydroxy-2H-1-benzothiopyran-3-carboxamide, 1,1-dioxide, mp 205°-208° C.

EXAMPLE 32

N-[4-[2-(2,5-Dimethoxyphenyl)ethyl]phenyl]-4-hydroxy-2H-1-benzothiopyran-3-carboxamide, 1,1-dioxide, mp 180°-181° C.

EXAMPLE 33

N-[4-[2-(3,5-Dihydroxyphenyl)ethyl]phenyl]-4-hydroxy-2H-1-benzothiopyran-3-carboxamide, 1,1-dioxide, mp 237° C. (dec)

EXAMPLE 34

N-[4-[2-(3,5-Dimethoxyphenyl)ethyl]phenyl]-4-hydroxy-2H-1-benzothiopyran-3-carboxamide, 1,1-dioxide, mp 201-202

EXAMPLE 35

4-Hydroxy-N-[4-[2-(3,4,5-trimethoxyphenyl)ethyl]phenyl-2H-1-benzothiopyran-3-carboxamide, 1,1-dioxide, mp 175°-177° C.

EXAMPLE 36

4-Hydroxy-N-[4-[2-(3,4,5-trihydroxyphenyl)ethyl]phenyl-2H-1-benzothiopyran-3-carboxamide, 1,1-dioxide, mp 152° C. (dec)

EXAMPLE 37

4-Hydroxy-N-8 4-[2-(2-methoxyphenyl)ethyl]phenyl-2H-1-benzothiopyran-3-carboxamide, 1,1-dioxide, mp 189°-191° C.

EXAMPLE 38

4-Hydroxy-N-[4-[2-(2-hydroxyphenyl)ethyl]phenyl-2H-1-benzothiopyran-3-carboxamide, 1,1-dioxide, mp 219°-220° C.

EXAMPLE 39

3,4-Dihydro-N-[4-[2-(3-methoxyphenyl)ethyl]phenyl-4-oxo-2H-1-benzothiopyran-3-carboxamide, 1,1-dioxide, mp 189°-190° C.

EXAMPLE 40

3,4-Dihydro-N-[4-[2-(4-hydroxyphenyl)ethyl]phenyl-4-oxo-2H-1-benzothiopyran-3-carboxamide, 1,1-dioxide, mp 235°-237° C.

EXAMPLE 41

3,4-Dihydro-N-[4-[2-(4-methoxyphenyl)ethyl]phenyl-4-oxo-2H-1-benzothiopyran-3-carboxamide, 1,1-dioxide, mp 223°-225° C.

EXAMPLE 42

N-[4-[2-(2-Chlorophenyl)ethyl]phenyl]-4-hydroxy-2H-1-benzothiopyran-3-carboxamide, 1,1-dioxide, mp 226°-229° C.

EXAMPLE 43

4-Hydroxy-N-[4-[2-(2-methylphenyl)ethyl]phenyl-2H-1-benzothiopyran-3-carboxamide, 1,1-dioxide, mp 209°-211° C.

EXAMPLE 44

3,4-Dihydro-4-oxo-N-[4-[2-(4-(trifluoromethyl)phenyl)ethyl]phenyl-2H-1-benzothiopyran-3-carboxamide, 1,1-dioxide, mp 223°-224° C.

EXAMPLE 45

3,4-Dihydro-N-[4-[2-(4-methylphenyl)ethyl]phenyl-4-oxo-2H-1-benzothiopyran-3-carboxamide, 1,1-dioxide, mp 213°-216° C.

EXAMPLE 46

N-[4-[2-([1,1'-biphenyl]-4-yl)ethyl]phenyl]-3,4-dihydro-4-oxo-2H-1-benzothiopyran-3-carboxamide, 1,1-dioxide, mp 248°–252° C.

EXAMPLE 47

4-[2-[4-[[(3,4-Dihydro-4-oxo-2H-1-benzothiopyran-3-yl)carbonyl]amino]pheyl]ethyl]benzoic acid, ethyl ester, 1,1-dioxide, 213°–215° C.

EXAMPLE 48

N-[4-[2-(4-Butoxyphenyl)ethyl]phenyl-3,4-dihydro-4-oxo-2H-1-benzothiopyran-3-carboxamide, 1,1-dioxide, mp 185°–187° C.

EXAMPLE 49

N-[4-[2-(4-(Acetylamino)phenylethyl]phenyl]-3,4-dihydro-4-oxo-2H-1-benzothiopyran-3-carboxamide, 1,1-dioxide, mp 256°–258° C.

EXAMPLE 50

N-[4-[2-(3-Acetylamino-4-methoxy)ethyl]phenyl]-3,4-dihydro-4-oxo-2H-1-benzothiopyran-3-carboxamide, 1,1-dioxide, mp 255°–258° C.

EXAMPLE 51

4-Hydroxy-N-[4-[2-(2-naphthalenyl)ethyl]phenyl]-2H-1-benzothiopyran-3-carboxamide, 1,1-dioxide, mp 222°–225° C.

EXAMPLE 52

N-[4-[2-(4-Aminophenyl)ethyl]phenyl]-3,4-dihydro-4-oxo-2H-1-benzothiopyran-3-carboxamide, 1,1-dioxide, mp 210°–245° C.

EXAMPLE 53

N-[4-[2-(3,4-Dimethylphenyl)ethyl]phenyl]-3,4-dihydro-4-oxo-2H-1-benzothiopyran-3-carboxamide, 1,1-dioxide, mp 207°–209° C.

EXAMPLE 54

N-[4-[2-(4-Chlorophenyl)ethyl]phenyl]-3,4-dihydro-4-oxo-2H-1-benzothiopyran-3-carboxamide, 1,1-dioxide, mp 242–245

EXAMPLE 55

N-[4-[2-[4-(Dimethylaminophenyl)ethyl]phenyl]-3,4-dihydro-4-oxo-2H-1-benzothiopyran-3-carboxamide, 1,1-dioxide.HCl, mp 234°–237° C.

EXAMPLE 56

N-[2-[2-(3,4-Dihydroxyphenyl)ethyl]phenyl]-4-hydroxy-2H-1-benzothiopyran-3-carboxamide, 1,1-dioxide, mp 195°–210° C.

EXAMPLE 57

N-[2-[2-[3,4-Dimethoxyphenyl)ethyl]phenyl]-4-hydroxy-2H-1-benzothiopyran-3-carboxamide, 1,1-dioxide, mp 192°–196° C.

EXAMPLE 58

N-(4-Hexylphenyl)-3,4-dihydro-4-oxo-2H-1-benzothiopyran-3-carboxamide, 1-1-dioxide, mp 169.5°–170° C.

EXAMPLE 59

3,4-Dihydro-N-(4-octylphenyl)-4-oxo-2H-1-benzothiopyran-3-carboxamide, 1,1-dioxide, mp 169°–170° C.

EXAMPLE 60

N-(4-Decylphenyl)-3,4-dihydro-4-oxo-2H-1-benzoothiopyran-3-carboxamide, 1,1-dioxide, mp 156°–158° C.

EXAMPLE 61

N-(4-Dodecylphenyl)-3,4-dihydro-4-oxo-2H-1-benzothiopyran-3-carboxamide, 1,1-dioxide, mp 156°–158° C.

EXAMPLE 62

N-[4-[2-(3-Trifluoromethylphenyl)ethyl]phenyl]-4-hydroxy-2H-1-benzothiopyran-3-carboxamide, 1,1-dioxide, mp 188°–195° C.

EXAMPLE 63

N-[4-[2-[3,5-bis-Trifluoromethyl(phenyl)]ethyl]phenyl]-4-hydroxy-2H-1-benzothiopyran-3-carboxamide, 1,1-dioxide, mp 232°–234° C.

EXAMPLE 64

N-[4-[2-(2,3,4,5,6-Pentafluorophenyl)ethyl]phenyl]-4-hydroxy-2H-1-benzothiopyran-3-carboxamide, 1,1-dioxide, 216°–218° C.

EXAMPLE 65

N-[4-[2-(3,4-Dihydroxyphenyl)ethyl]phenyl]-4,6-dihydroxy-2H-benzothiopyran-3-carboxamide, 1,1-dioxide, mp 234°–235° C.

EXAMPLE 66

2H-1-Benzothiopyran-3-carboxamide, N-[4-[2-(4-aminophenyl)ethenyl]phenyl]-3,4-dihydro-4-oxo-, 1,1-dioxide, mp>300 C.

EXAMPLE 67

2H-1-Benzothiopyran-3-carboxamide, 3,4-dihydro-N-[4-[2-(4-nitrophenyl)ethenyl]phenyl]-4-oxo-, 1,1-dixide, mp 262°–266° C.

EXAMPLE 68

2H-1-Benzothiopyran-3-carboxamide, N-[4-[2-(3-chlorophenyl)ethyl]phenyl]-4-hydroxy-, 1,1-dioxide, mp 195°–197° C.

EXAMPLE 69

2H-1-Benzothiopyran-3-acetamide,

N-[4-[2-(3,4-dichlorophenyl)ethyl]phenyl]-4-hydroxy-

α-oxo-, 1,1-dioxide, mp 197° C. (dec)

EXAMPLE 70

2H-1-Benzothiopyran-3-carboxamide,
4-hydroxy-N-[4-[2-(4-hydroxy-3-methoxyphenyl)ethyl]phenyl]-, 1,1-dioxide, mp 225°–228° C.

EXAMPLE 71

2H-1-Benzothiopyran-3-carboxamide,
N-[4-[2-(3,5-dichlorophenyl)ethyl]phenyl]-4-hydroxy-, 1,1-dioxide, mp 206°–210° C.

EXAMPLE 72

2H-1-Benzothiopyran-3-carboxamide,
N-[4-[2-(2,4-dichlorophenyl)ethyl]phenyl]-4-hydroxy-1,1-dioxide, mp 227°–32° C.

EXAMPLE 73

2H-1-Benzothiopyran-3-carboxamide,
4-hydroxy-N-[4-[2-(1-naphthalenyl)ethyl]phenyl], 1,1-dioxide, mp 214°–5·°C.

EXAMPLE 74

2H-1-Benzothiopyran-3-carboxamide,
N-[4-[2-(3,4-dichlorophenyl)ethenyl]phenyl]-4-hydroxy-, 1,1-dioxide, mp 264°–268° C.

EXAMPLE 75

2H-1-Benzothiopyran-3-carboxamide,
4-hydroxy-N-[4-[2-(4-phenoxyphenyl)ethyl]phenyl]-, 1,1-dioxide, mp 168°–72° C.

EXAMPLE 76

2H-1-Benzothiopyran-3-carboxamide,
N-[3-[2-(3,4-dichlorophenyl)ethyl]phenyl]-4-hydroxy-, 1,1-dioxide, mp 181°–183° C.

EXAMPLE 77

2H-1-Benzothiopyran-3-carboxamide,
N-[4-[2-[3,5-bis(1,1-dimethylethyl)-4-hydroxyphenyl]ethyl]phenyl]-4-hydroxy-, 1,1-dioxide, mp 213°–5° C.

EXAMPLE 78

2H-1-Benzothiopyran-3-carboxamide,
N-[4-[(3,4-dichlorophenyl)methyl]phenyl]-4-hydroxy-, 1,1-dioxide, mp 203°–200° C.

EXAMPLE 79

2H-1-Benzothiopyran-3-carboxamide,
N-[4-[3-(3,4-dichlorphenyl)propyl]phenyl]-4-hydroxy-, 1,1-dioxide, mp 168°–170° C.

EXAMPLE 80

2H-1-Benzothiopyran-3-carboxamide,
N-[2-[3-(3,4-dichlorophenyl)propyl]phenyl]-4-hydroxy-, 1,1-dioxide, mp 180°–182° C.

EXAMPLE 81

2H-1-Benzothiopyran-3-carboxamide,
N-[2-[(3,4-dichlorophenyl)methyl]phenyl]-4-hydroxy, 1,1-dioxide, mp 205°–207° C.

EXAMPLE 82

2H-1-Benzothiopyran-3-carboxamide,
3,4-dihydro-N-[4-[2-(3-hydroxyphenyl)ethyl]phenyl-4-oxo, 1,1-dioxide, mp 224°–225° C.

V. Preparation of Compounds of Formula I Wherein Q is $I_2$

Compounds of Formula II wherein Q is $I_2$ are prepared in accordance with the conditions detailed in U.S.

Pat. No. 3,591,584 cited above and used as shown in Scheme I to prepare the compounds of Formula I wherein Q is I$_2$. Representative examples are as follows.

EXAMPLE 83

N-[4-[2-(3,4-Dimethoxyphenyl)ethyl)phenyl]-4-hydroxy-2-methyl-2H-1,2-benzothiazine-3-carboxamide, 1,1-dioxide (See Scheme I, Formula I Wherein Q is I$_2$ Wherein b is zero, Y is 1, R$_5$ is H; Z is methyl, R$_6$ is 2-(3,4-dimethoxyphenyl)ethyl)

A mixture of methyl 4-hydroxy-2-methyl-2H-1,2-benzothiazine-3-carboxylate 1,1-dioxide (J. D. Genzer and F. C. Fontsere, U.S. Pat. No. 3,960,856 (1976)) (5.9 g, 0.022 mole) and 4-[2-(3,4-dimethoxyphenylethyl]benzenamine (5.6 g, 0.022 mole) in xylene (600 ml) is heated at reflux for 24 hours in a soxhlet apparatus, the thimble of which contains 20 g of Linde type 4A molecular sieve. The reaction mixture is allowed to cool when the product crystallized out. The product is filtered, washed with methanol, and dried to give 9.8 g of white crystals, mp 235°–8° C.

In a manner analogous to that found in Example 83 above using appropriate starting materials additional compounds are prepared as follows.

EXAMPLE 84

N-[4-[2-(3,4-dimethoxyphenyl)ethyl)phenyl]-4-hydroxy-2H-1,2-benzothiazine-3-carboxamide, 1,1-dioxide, mp 201°–205° C.

EXAMPLE 85

N-[2-[2-(3,4-dimethoxyphenyl)ethyl)phenyl]-4-hydroxy-2-methyl-2H-1,2-benzothiazine-3-carboxamide, 1,1-dioxide, mp 130°–135° C.

EXAMPLE 86

N-[4-[2-(3,4-dichlorophenyl)ethyl]phenyl]-4-hydroxy-2-methyl-2H-1,2-benzothiazine-3-carboxamide, 1,1-dioxide, mp 260°–262° C.

EXAMPLE 87

2H-1,2-Benzothiazine-3-carboxamide, 4-hydroxy-N-[4-[2-(4-hydroxy-3-methoxyphenyl)ethenyl]phenyl]-2-methyl, 1,1-dioxide, mp 257°–259° C.

EXAMPLE 88

2H-1,2-Benzothiazine-3-carboxamide, 4-hydroxy-N-[4-[2-(4-hydroxy-3-methoxyphenyl)ethyl]phenyl]-2-methyl-, 1,1-dioxide, mp 231°–231.5° C.

EXAMPLE 89

N-[4-[2-(3,4-dihydroxyphenyl)ethyl]phenyl]-4-hydroxy-2-methyl-2H-1,2-benzothiazine-3-carboxamide, 1,1-dioxide (see Scheme I, Formula I Wherein Q is I$_2$, Wherein b is zero, Z is Methyl, R$_5$ is hydrogen, R$_6$ is 2-(3,4-dihydroxyphenyl)ethyl)

A cold (0°–10° C.) mixture of N-[4-[2-(3,4-dimethoxyphenyl)ethyl)phenyl]-4-hydroxy-2-methyl-2H-1,2-benzothiazine-3-carboxamide, 1,1-dioxide (19.8 g, 0.04 mole) and methylene chloride (1000 ml) is treated slowly with boron tribromide (100 g; 0.4 mole) during 30 minutes. The yellow-green solution is allowed to warm up to room temperature when a precipitate is formed. The reaction mixture is stirred at room temperature for 4.5 hours and then slowly poured into 30 l of ice water and stirred for 45 minutes. The precipitated solid is filtered, washed with water, and dried. The crude product is then triturated with hot methanol and filtered to give a white solid (15.6 g; 83%), mp 257°–9° C. dec.

In a manner analogous to that found in Example 86 above using appropriate starting materials an additional compound is prepared as follows.

EXAMPLE 90

N-[2-[2-(3,4-Dihydroxyphenyl)ethyl]phenyl]-4-hydroxy-2-methyl-2H-1,2-benzothiazine-3-carboxamide, 1,1-dioxide, mp 178°–180° C.

VI. Preparation of Compounds of Formula I Wherein Q is I$_3$

A. Intermediates of Formula XII and XXIII.

Intermediates of the Formula XIII or XXIII as shown in Scheme VI to be useful in the preparation of compounds of Formula I wherein Q is I$_3$ are prepared from the compounds of Formula III in a manner shown in Scheme X and exemplified as follows.

EXAMPLE 91

N'-[4-[2-(3,4-Dimethoxyphenyl)ethyl]phenyl-N,N-diphenyl urea (see Formula XIII in Scheme VI Wherein R$_5$ is hydrogen and R$_6$ is 4-[2-(3,4-dimethoxyphenyl)ethyl])

A mixture of 30.0 g (0.12 mole) of 4-[2-(3,4-dimethoxyphenyl)ethyl]benzenamine (as prepared in Preparation 1 above), 24.7 g (34 ml, 0.24 mole) of triethylamine, and 27.0 g (0.12 mole) of diphenylcarbamyl chloride in 180 ml of absolute ethanol was stirred at reflux for 17 hours. The cooled reaction mixture was evaporated, and the residue was partitioned between dichloromethane (600 ml) and water (400 ml). The organic layer was washed with 1N hydrochloric acid (3×400 ml), brine (1×400 ml), dried (sodium sulfate), and evaporated. Recrystallization of the residue from ethyl acetate/hexane yielded 44.9 g (82% yield) of the urea product, mp 113°–115° C.

EXAMPLE 92

N-[4-[2-(4-Methoxyphenyl)ethyl]phenyl-N,N-diphenyl urea (See Scheme VI, Formula XIII Wherein R$_5$ is hydrogen and R$_6$ is 4-[2-(4-methoxyphenyl)ethyl]

A mixture of 60.0 g (0.26 mole) of 4-[2-(4-methoxyphenyl)ethyl]benzenamine (L. A. Strait, D. Jambotkar, R. Ketcham, and M. Hrenoff, *J. Org. Chem.*, 31, 3976 (1966)), 55.7 g (77 ml; 0.55 mole) of triethylamine, and 61.2 g (0.26 mole) of diphenylcarbamyl chloride in 380 ml of absolute ethanol was stirred at reflux for 24 hours. The reaction mixture was cooled and the precipitated solid was filtered and washed with water. Recrystallization from ethanol yielded 96.4 g (86% yield) of the urea product, mp 121°–124° C.

EXAMPLE 93

N'-(4-Decylphenyl)-N,N-diphenyl urea (see Scheme VI, Formula XIII Wherein R$_5$ is hydrogen and R$_6$ is 4-decylphenyl)

Prepared by the procedure described in Example 92 above from 5.0 g (0.021 mole) of 4-decylbenzenamine. Recrystallization from methanol yielded 7.1 g (77% yield) of the urea product, mp 90°–91° C.

EXAMPLE 94

N'-(4-Dodecylphenyl)-N,N-diphenyl urea (See Scheme VI, Formula XIII Wherein $R_5$ is hydrogen and $R_6$ is 4-dodecylbenzenamine)

Prepared by the procedure described in Example 92 from 5.0 g (0.019 mole) of 4-dodecylbenzeamine. Recrystallization from methanol yielded 6.7 g (77% yield) of the urea product, mp 92°–94° C.

EXAMPLE 95

N'-[4-[2-(3,4-Dichlorophenyl)ethyl]phenyl-N,N-diphenyl urea (See Scheme VI, Formula XIII Wherein $R_5$ is hydrogen and $R_6$ is 4-[2-(3,4-dichlorophenyl)ethyl])

Prepared by the procedure described in Example 92 from 3.0 g (0.011 mole) of 4-[2-(3,4-dichlorophenyl)ethyl]benzenamine. There was obtained 4.5 g (86%) of the urea product, mp 153°–155° C.

EXAMPLE 96

N'-[4-[2-(4-Chlorophenyl)ethyl]phenyl-N,N-diphenyl urea (See Scheme VI, Formula XIII Wherein R is hydrogen and $R_6$ is 4-[2-(4-chlorophenyl)ethyl])

Prepared by the procedure described in Example 92 from 3.0 g (0.013 mole) of 4-[2-(4-chlorophenyl)ethyl]benzenamine (*Chem. Abstrs.*, 93, 63,603q (1980)). Recrystallization from methanol yielded (54% yield) of the urea product, mp 180°–182° C.

EXAMPLE 97

[4-[2-(3,4-Dichlorophenyl)ethyl]phenylamino]-oxoacetic acid ethyl ester (See Scheme VI, Formula XXIII Wherein $R_5$ is hydrogen and $R_6$ is 4-[2-(3,4-dichlorophenyl)ethyl])

A mixture of 32.9 g (0.12 mole) of 4-[2-(3,4-dichlorophenyl)ethyl]benzeamine, and 22.5 g (31 ml, 0.22 mole) of triethylamine in 75 ml of N,N-dimethylformamide was cooled in ice and treated over 20 minutes with 21.4 g (17.5 ml, 0.16 mole) of ethyl oxalyl chloride. After one hour, the ice bath was removed, and the mixture was stirred for an additional 24 hours. The reaction mixture was added to 1.0 kg ice/water, and the precipitated solid was filtered and washed with water. Recrystallization from methanol/N,N-dimethylformamide/water yielded 41.3 g (91% yield) of the amide product, mp 128°–130° C.

EXAMPLE 98

[(4-Decylphenyl)amino]-oxo-acetic acid ethyl ester (See Scheme VI, Formula XIII Wherein $R_5$ is hydrogen and $R_6$ is 4-decyphenyl Prepared by the procedure described in Example 99 from 4-decylbenzenamine (9.3 g, 0.040 mole). Recrystallization from methanol/water yielded 10.2 g (77% yield) of the amide product, mp 56°–58° C.

EXAMPLE 99

[4-[2-(3,4-Dimethoxyphenyl)ethyl]phenylamino]-oxoacetic acid ethyl ester (See Scheme VI, Formula XXIII Wherein $R_5$ is hydrogen and $R_6$ is 4-[2-(3,4-dimethoxyphenyl)ethyl]

Prepared by the procedure described in Example 97 from 4-[2-(3,4-dimethoxyphenyl)ethyl]benzenamine (15.3 g, 0.059 mole). Recrystallization from methanol water yielded 18.6 g (88% yield) of the amide product, mp 122°–124° C.

B. Compounds of Formula I Wherein Q is $I_3$

For compounds of Formula I having Q equal to $I_3$ the preparation is shown in Scheme VI where the compounds of Formula $XII_3$ are reacted with XIII or XXIII. The preparation is exemplified as follows.

EXAMPLE 100

2-Benzofurancarboxamide, N-[4-[2-(3,4-Dimethoxyphenyl)ethyl]phenyl]-2,3-dihydro-7-methoxy-3-oxo-(See Scheme VI, Formula I wherein y is one, Q is $I_3$, Wherein $R_1$ is 7-methoxy, b is one, $R_5$ is hydrogen, and $R_6$ is 4-[2-(3,4-dimethoxyphenyl)ethyl]

A mixture of 1.8 g (0.038 mole) of 50% sodium hydride mineral oil suspension in 100 ml of N,N-dimethylformamide under a nitrogen atmosphere was stirred and cooled in ice. To the mixture was added over 30 minutes, 5.5 g (0.034 mole) of 7-methoxy-3-[2H]-benzofuranone. After stirring for an additional one hour, 15.8 g (0.037 mole) of N'-[4-[2-(3,4-dimethoxyphenyl)ethyl]-phenyl-N,N-diphenyl urea as prepared in Example 91 above was added, and the ice bath was removed. The mixture was stirred for 48 hours, added to 700 g ice/water, and acidified with acetic acid. The precipitated solid was filtered, washed with water, and recrystallized from 2-methoxyethanol/water to yield 9.1 g (61% yield) of the amide product, mp 173°–175° C.

In a manner analogous to the above Example 100 using appropriate starting materials the following compounds are prepared.

EXAMPLE 101

Naphtho[2,3-b]furan-2-carboxamide,
N-[4-[2-(3,4-dimethoxyphenyl)ethyl]phenyl]-2,3-dihydroxy-3-oxo, mp 220°–223° C.

EXAMPLE 102

2-Benzofurancarboxamide,
N-[4-[2-(3,4-dimethoxyphenyl)ethylphenyl)-3-hydroxy, mp 175°–176° C.

EXAMPLE 103

Naptho[2,1-b]furan-2-carboxamide,
1-hydroxy-N-[4-[2-(3,4-dimethoxyphenyl)ethyl]phenyl], mp 176°–179° C.

EXAMPLE 104

Naphtho[2,3-b]furan-2-carboxamide,
N-(4-dodecylphenyl)-3-hydroxy, mp 182°–184° C.

EXAMPLE 105

2-Benzofurancarboxamide,
N-(4-dodecylphenyl)-3-hydroxy mp 154°–156° C.

EXAMPLE 106

Naphtho[1,2-b]furan-2-carboxamide,
N-[4-[2-(3,4-dimethoxyphenyl)ethyl]phenyl]-2,3-dihydro-3-oxo, mp 172°–174° C.

EXAMPLE 107

2-Benzofurancarboxamide,
N-(4-decylphenyl)-3-hydroxy, mp 161°–162° C.

EXAMPLE 108

Naphtho[2,3-b]furan-2-carboxamide,
N-(4-decylphenyl)-3-hydroxy, mp 185°–188° C.

EXAMPLE 109

Naptho[2,1-b]furan-2-carboxamide,
N-[4-[2-(3,4-dimethylphenyl)ethyl]phenyl]-1-hydroxy A mixture of 1.88 g (2.6 ml, 0.019 mole) of diisopropylamine in 20 ml of tetrahydrofuran under a nitrogen atmosphere was cooled to 0° to −10° C. in an ice/sodium chloride cooling bath. The mixture was stirred and treated over 20 minutes with a solution of 8.8 ml (0.019 mole) of n-butyl lithium (2.1M in n-hexane) at a rate that allowed the reaction mixture to remain at <0° C. The mixture was stirred for an additional 20 minutes, and then a solution of 1.95 g (0.087 mole) of 4-[2-(3,4-dimethylphenyl)ethyl]benzenamine in 20 ml of tetrahydrofuran was added over 15 minutes. After stirring for an additional 20 minutes, a solution of 2.0 g (0.083 mole) of 1,2-dihydro-1-oxo-naphtho[2,1-b]furan-2-carboxylic acid methyl ester (preparation for the isomeric naphtho[2,3-b]furan ester described by P. Emmott and R. Livingstone, *J. Chem. Soc.*, 4629 (1958)) in 20 ml of tetrahydrofuran was added over 20 minutes. The mixture was stirred as the cooling bath was allowed to slowly melt over 18 hours. The reaction mixture was added to 600 g of ice water containing 8.0 ml of concentrated hydrochloric acid. After stirring for two hours, the precipitated solid was filtered, washed with water, and recrystallized from 2-propanol/N,N-dimethylformamide/water to yield 1.0 g (28% yield) of the amide product, mp 188°–191° C.

In a manner analogous to that described above in Example 109 there was also prepared:

EXAMPLE 110

Naphtho[2,1-b]furan-2-carboxamide,

N-[4-[2-(4-hydroxy-3-methoxyphenyl)ethyl]phenyl]-

1,2-dihydro-1-oxo, mp 189°–191° C.

By employing 4-[2-(4-hydroxy-3-methoxyphenyl)ethyl]benzenamine as the amine, plus an additional equivalent amount of diisopropylamine and n-butyl lithium in order to complex with the amine hydroxyl group during reaction.

EXAMPLE 111

2-Benzofuranacetamide,

N-[4-[2-(3,4-Dimethoxyphenyl)ethyl]phenyl]-2,3-dihydro-7-methoxy-α,3-dioxo-(See Scheme VI, Formula I Wherein y is 2, Q is $I_3$; Wherein b is one, $R_1$ is 7-methoxy, $R_5$ is hydrogen, and $R_6$ is 4-[2-(3,4-dimethoxyphenyl]ethyl])

Prepared by the procedure described in Example 109 from 6.3 g (0.038 mole) of 7-methoxy-3[2H]-benzofuranone, except that [4-[2-(3,4-dimethoxyphenyl)ethyl]-phenylamino]-oxo-acetic acid ethyl ester (15.1 g, 0.042 mole) was employed as the acylating agent rather than the mixed urea used in Example 109. Recrystallization of the final product from N,N-dimethylformamide/water yielded 7.5 g (41% yield) of the amide product, mp 242°–245° C.

In a manner analogous to Example 111 above using appropriate starting materials the following compounds are prepared.

EXAMPLE 112

Naphtho[2,1-b]furan-2-acetamide, N-[4-[2-(3,4-dimethoxyphenyl)ethyl]phenyl]-1-hydroxy-α-oxo, mp 229°–230° C.

EXAMPLE 113

Naphtho[2,3-b]furan-2-acetamide, N-[4-[2-(3,4-dichlorophenyl)ethyl]phenyl]-3-hydroxy-α-oxo, mp 271°–273° C.

EXAMPLE 114

Naphtho[1,2-b]furan-2-acetamide, N-[4-[2-(3,4-dimethoxyphenyl)ethyl]phenyl]-3-hydroxy-α-oxo, mp 225°–231° C.

EXAMPLE 115

2-Benzofuranacetamide, N-[4-[2-(3,4-dimethoxyphenyl)ethyl]phenyl]-3-hydroxy-5,6-dimethoxy-α-oxo, mp 248°–250° C.

EXAMPLE 116

2-Benzofuranacetamide, N-(4-decylphenyl)-2,3-dihydro-α,3-dioxo, mp 175°–178° C.

EXAMPLE 117

Naptho[2,3-b]furan-2-acetamide, N-[4-[2-(3,4-dimethoxyphenyl)ethyl]phenyl]-2,3-dihydro-α,3-dioxo, mp 244°–246° C.

EXAMPLE 118

2-Benzofuranacetamide, N-[4-[2-(3,4-dichlorophenyl)ethyl]phenyl-2,3-dihydro-α,3-dioxo, 245° C. dec

EXAMPLE 119

2-Benzofuranacetamide, N-[4-decylphenyl]-3-hydroxy-5,6-dimethoxy-α-oxo, mp 187°–188° C.

EXAMPLE 120

Naphtho[2,3-b]furan-2-acetamide, N-[4-decylphenyl]-2,3-dihydro-α,3-dioxo, mp 218°–221° C.

EXAMPLE 121

2-Benzofuranacetamide, N-[4-[2-(3,4-dimethoxyphenyl)ethyl]phenyl]-3-hydroxy-α-oxo, mp 238°–240° C.

Ether cleavage to obtain compounds corresponding to hydroxy bearing compounds are exemplified hereafter.

EXAMPLE 122

Naphtho[2,1-b]furan-2-carboxamide, N-[4-[2-(3,4-dihydroxyphenyl)ethyl]phenyl]-1-hydroxy- A mixture of 19.5 g (0.062 mole) of boron tribromide dimethyl sulfide complex in 300 ml of 1,2-dichloroethane under a nitrogen atmosphere, was cooled in ice and treated with 6.0 g (0.013 mole) of N-[4-[2-(3,4-dimethoxyphenyl)ethyl]phenyl]-1-hydroxynaphtho[2,1-b]furan-2-carboxamide as prepared in Example 103 above. The mixture was stirred at reflux for 18 hours, cooled, and added to 1.0 kg ice/water. After stirring for several hours, the emulsion was extracted with ethyl acetate (3×750 ml), and the organic layers were combined, dried (sodium sulfate), and evaporated. Recrystallization of the residue from methanol/N,N-dimethylformamide/water yielded 2.5 g (44% yield) of the catechol product, mp 214°–216° C.

In a manner analogous to Example 122 above using appropriate starting materials the following compounds are prepared.

EXAMPLE 123

2-Benzofuranacetamide, N-[4-[2-(3,4-dihydroxyphenyl)ethyl]phenyl]-3-hydroxy-7-methoxy-α-oxo, 0.25 H$_2$O, mp 260° C. dec

EXAMPLE 124

2-Benzofurancarboxamide, N-[4-[2-(3,4-dihydroxyphenyl)ethyl]phenyl]-3-hydroxy, mp 208°–209° C.

EXAMPLE 125

Naphtho[1,2-b]furan-2-carboxamide, N-[4-[2-(3,4-dihydroxyphenyl)ethyl]phenyl]-3-hydroxy, 0.5 H$_2$O, mp 180°–185° C.

EXAMPLE 126

2-Benzofuranacetamide, N-[4-[2-(3,4-Dihydroxyphenyl)ethyl]phenyl]-2,3-dihydro-α,3-dioxo- (See Scheme VI, Formula I Wherein y is 2; Q if I$_3$ Wherein R$_1$ is Hydrogen; R$_5$ is Hydrogen; R$_6$ is 4-[2-(3,4-dihydroxyphenyl)ethyl]

A mixture of 4.3 g (0.0097 mole) of N-[4-[2-(3,4-dimethoxyphenyl)ethyl]phenyl]-3-hydroxy-α-oxo-2-benzofuranacetamide as prepared in Examples 121 above in 250 ml of dichloromethane under a nitrogen atmosphere was cooled to −78° C. To the mixture was added 46 ml (0.046 mole) of 1.0M solution of boron tribromide in dichloromethane. The mixture was stirred for four hours at −78° C., and then for 22 hours with the cooling bath removed. The mixture was recooled to −10° C. and 200 ml of cold water was added. After stirring for several hours, the insoluble material was filtered and washed with water. The crude product was digested on the steam bath for 90 minutes in 800 ml of 50% aqueous methanol. The mixture was cooled and the insoluble material again filtered and washed with water. Recrystallization from tetrahydrofuran/ethanol yielded 2.3 g (58% yield) of the catechol product, mp 231°–232° C.

In a manner analogous to above Example 126 using appropriate starting materials the following compounds are prepared.

EXAMPLE 127

2-Benzofuranacetamide,
N-(4-decylphenyl)-3,5,6-trihydroxy-α-oxo, 278°–280° C. dec

EXAMPLE 128

Naphtho[2,3-b]furan-2-carboxamide,
N-[4-[2-(3,4-dihydroxyphenyl)ethyl]phenyl]-3-hydroxy, 1H$_2$O, mp 165°–169° C.

EXAMPLE 129

Naphtho[2,3-b]furan-2-acetamide,
N-[4-[2-(3,4-dihydroxyphenyl)ethyl]-2,3-dihydro-α,3-dioxo, 0.2H$_2$O, mp 278°–281° C.

EXAMPLE 130

2-Benzofuranacetamide,
N-[4-[2-(3,4-Dihydroxyphenyl)ethyl]phenyl]-3,5,6-trihydroxy-α-oxo, mp 282°–284° C. dec VII. Preparation of Compounds of Formula I Wherein Q is I$_4$ For compounds of Formula I wherein Q is equal to I$_4$ the preparation as shown in Scheme I is examplified as follows.

EXAMPLE 131

N-[4-[2-(3,4-Dimethoxyphenyl)ethyl]phenyl]-3-hydroxy-α-oxo-benzo[b]thiophene-2-acetamide (See Scheme I, Formula I, Wherein Q is I$_4$, Wherein b is zero; y is 2; R$_5$ is hydrogen; R$_6$ is 4-[2-(3,4-dimethoxyphenyl)ethyl])

To a stirred solution of benzo[b]thiophene-2-acetic acid, 3-hydroxy-α-oxo (Fries and Bartholomaus, Annalen, 405, 391 (1914)) (44.44 g, 0.2 mole) and 4-(3,4-dimethoxyphenethyl)aniline (51.46 g, 0.2 mole) in methylene chloride (2.5 l) and tetrahydrofuran (1 l) under nitrogen at −7° C. is added a solution of dicyclohexycarbodiimide (41.7 g, 0.202 mole) in methylene chloride (200 ml) over a period of 55 minutes. The mixture is stirred at −7° to 0° C. for two hours and at room temperature overnight. The precipitate is collected by filtration and washed with methylene chloride to give a solid, consisting of the product and dicyclohexylurea. Evaporation of the mother liquor under reduced pressure below 45° C. gives a solid, which is combined with the first crop, dissolved in ~4 l of boiling chloroform and left at room temperature overnight. Dicyclohexylurea (26 g) is removed by filtration and the filtrate is chromatographed on 1 kg of silica gel. Elution with chloroform gives 61.4 g of a solid. Recrystallization from tetrahydrofuran yields 53.2 g (57.6%) of a light-yellow crystalline solid, mp 204°–205° C.

EXAMPLE 132

N-[4-[2-(3,4-Dimethoxyphenyl)ethyl]phenyl]-3-hydroxy-α-oxo-benzo[b]thiophene-2-acetamide
(Alternate preparation of the same compound as in Example 131)

To a stirred solution of diisopropylamine (3.3 g, 0.03 mole) in dry tetrahydrofuran (20 ml) cooled to 0° C. is added streamwise under nitrogen n-butyllithium (13.05 ml, 0.03 mole; 2.3M solution of n-butyl lithium in hexane). After the addition the solution is allowed to stir at ice bath temperature for 15 minutes and then a solution of 4-(3,4-dimethoxyphenethyl)aniline (3.08 g, 0.012 mole) in tetrahydrofuran (30 ml) is added. The greenish colored solution is stirred in an ice bath for 18 minutes and a solution of benzo[b]thiophene-2-acetic acid-3-hydroxy-α-oxo-methylester (Bo Lamm and Carl-Johan Aurell, Acta Chemica Scandinavica, Ser. B., 36(7), 435–42 (1982)) (2.36 g, 0.01 mole) in tetrahydrofuran (35 ml) is added. The yellow colored solution is stirred at ice bath temperature for 15 minutes and then at room temperature for one hour. The mixture is poured into 10% aqueous hydrochloric acid (300 ml) and the solid is filtered off, washed with hydrochloric acid (~200 ml), with water, and dried to give 4.5 g (90.2%) of a solid, mp 203°–04° C.

Recrystallization from tetrahydrofuran gives 3.2 (69.6%) of a light-yellow crystalline solid, mp 204°–205° C.

EXAMPLE 133

N-[4-[2-(3,4-Dihydroxyphenyl)ethyl]-3-hydroxy-α-oxo-benzo[b]thiophen-2-acetamide (See Scheme I, Wherein Q is I$_4$, Wherein b is zero; y is 2, R$_5$ is hydrogen, and R$_6$ is 4-[2-(3,4-dihydroxyphenyl)ethyl])

To a stirred solution of benzo[b]thiophene-2-acetic acid, 3-hydroxy-α-oxo (28.01 g, 0.126 mole) and 4-(3,4-trimethylsilyloxyphenethyl)aniline (47.1 g, 0.126 mole) as prepared in Preparation 20 above in dry tetrahydrofuran (400 ml) under nitrogen at −8° to −5° C. is added a solution of dicyclohexylcarbodiimide (26.9 g, 0.12 mole) in tetrahydrofuran (200 ml) over a period of 35 minutes. After the addition is complete the mixture is allowed to attain room temperature overnight with stirring. Dicyclohexylurea (23.94 g) is removed by filtration and the filtrate is evaporated to dryness on a rotary evaporator below 55° C. The residue is dissolved in methylene chloride (700 ml) and the solution is kept for three days in a cooler. After removal of dicyclohexylurea (1.2 g) by filtration, the filtrate is chromatographed on silica gel (490 g). Elution of the column with methylene chloride, gives 60.8 g of a residue, which is refluxed in methanol (3.5 l), and 2N aqueous hydrochloric acid (75 ml) for 80 minutes with stirring. The solution is cooled. The solid is filtered off and washed with methanol to give 36.2 g (66.3%) of a light-yellow crystalline solid, mp 197199° C.

Additional 5.9 g (10.8%) of pure product, mp 196°–8° C. is obtained from the mother liquid.

The same compound as is prepared in Example 133 above is prepared in an alternate process as exemplified in the following example.

EXAMPLE 134

N-[4-[2-(3,4-Dihydroxyphenyl)ethyl]phenyl]-3-hydroxy-α-oxo-benzo[b]thiophene-2-acetamide Benzo[b]thiophene-2-acetamide, N-[4-[2-(3,4-dimethoxyphenyl)ethyl]phenyl]-3-hydroxy-60-oxo (29.8 g, 0.064 mole) in methylene chloride (1.4 l), is added dropwise at −70° C. boron trimbromide (0.325 mole, 325 ml of 1M solution in methylene chloride), over a period of one hour. The mixture is stirred at room temperature overnight. The mixture is cooled in acetone-dry ice and water (~750 ml) is added. The mixture is stirred at room temperature for two hours. The precipitate is filtered off and washed with water (~2.5 l). The resulting solid is dissolved in methanol (2.5 l), water (1 l), and refluxed on a steam bath for 2.5 hours. The methanol (~1.2 l) is distilled off and water (~1 ) is added. After refluxing for one hour, the warm mixture is filtered. The residue is washed with water and dried. The solid is recrystallized from methanol to give 17.45 g (62.3%) of a light-yellow crystalline solid, mp 193°–5° C.

In a manner again analogous to Example 131 or 132 the following compounds are prepared using appropriate starting material.

EXAMPLE 135

Benzo[b]thiophene-2-acetamide, 5-chloro-N-(4-decylphenyl)-3-hydroxy-α-oxo, mp 145°–146° C.

EXAMPLE 136

Benzo[b]thiophene-2-acetamide, N-[4-[2-(3,4-dichlorophenyl)ethyl]phenyl]-3-hydroxy-α-oxo, mp 220°–221° C.

EXAMPLE 137

Beno[b]thiophene-2-acetamide, N-[4-[2-(4-chlorophenyl)ethyl]phenyl]-3-hydroxy-α-oxo, mp 210°–212° C.

In a manner analogous to Example 134 using the appropriate starting materials for example, prepared in Example 132, the following compound is prepared.

EXAMPLE 138

Benzo[b]thiophene-2-acetamide, 5-chloro-N-[4-[2-(3,4-dihydroxyphenyl)ethyl]phenyl]-3-hydroxy-α-oxo, mp 248° C. dec In a manner analogous to Example 132 using the appropriate starting materials, the following compound is prepared.

EXAMPLE 139

Benzo[b]thiophene-2-acetamide, 5-chloro-N-[4-[2-(3,4-dimethoxyphenyl)ethyl]phenyl]-3-hydroxy-α-oxo, mp 207°–209° C.

EXAMPLE 140

Benzo[b]thiophene-2-acetamide, 3-(acetyloxy)-N-[4-(2-(3,4-bis(acetyloxy)phenyl]ethyl)-phenyl]-α-oxo- To a stirred suspension of benzo[b]thiophene-2-acetamide, N-[4-[2-(3,4-dihydroxyphenyl)ethyl)phenyl]-3-hydroxy-α-oxo (14.9 g, 0.034 mole) in acetic anhydride (100 ml) under nitrogen below 25° C. is added dropwise pyridine (100 ml), then the mixture is stirred at room temperature for 21 hours. The suspension is poured on ice-water (~1.7 l) stirred for 30 minutes, and the precipitate is filtered off, washed with water, then dissolved in chloroform (~800 ml), washed with water (~1 l), dried with sodium sulfate, and the solvent is removed under reduced pressure on a rotary evaporator below 45° C., to give a solid in quantitative yield, mp 169°–170° C. Recrystallization from methylene chloride-methanol on cooling gives 17.16 g (87.4%) of a light-yellow crystalline solid, mp 170°–2° C.

EXAMPLE 141

Benzo[b]thiophene-2-acetamide, N-[4-[2-(3,4-bis)acetyloxy)phenyl)ethyl]phenyl]-3-hydroxy-α-oxo Prepared from 1,2-benzenediol, 4-[2-(aminophenyl)ethyl]diacetate (6.27 g, 0.02 mole), benzo[b]thiophene-2-acetic acid, 3-hydroxyα-oxo (4.44 g, 0.02 mole) and dicyclohexylcarbodiimide (4.13 g, 0.02 mole) in methylene chloride (500 ml) by the method of Example 112. Dicyclohexylurea is removed by filtration and the filtrate is chromatographed on 630 g of silica gel. Elution of the column with ethyl acetate gives 2.6 g of a solid. Recrystallization from methylene chloride-methanol gives 2.28 g (22%) of a light-yellow crystalline solid, mp 190°–2° C.

EXAMPLE 142

Benzo[b]thiophene-2-acetamide, 3-hydroxy-N-[4-[2-(4-hydroxy-3-methoxyphenyl)ethyl]phenyl]-α-oxo-, mp 189°–193° C.

EXAMPLE 143

Benzo[b]thiophene-2-carboxamide, N-[4-[2-(3,4-dimethoxphenyl)ethyl]phenyl]-3-hydroxy, mp 197°–198° C.

EXAMPLE 144

Benzo[b]thiophene-2-carboxamide, N-[4-[2-(3,4-dichlorophenyl)ethyl]phenyl-3-hydroxy, mp 193°–5° C.

EXAMPLE 145

Benzo[b]thiophene-2-carboxamide, N-[4-[2-(4-chlorophenyl)ethyl]phenyl]-3-hydroxy, mp 216°–220° C.

EXAMPLE 146

Benzo[b]thiophene-2-carboxamide, N-[3-[2-(3,4-dichlorophenyl)ethyl]phenyl]-3-hydroxy, mp 193°–195° C.

EXAMPLE 147

Benzo[b]thiophene-2-carboxamide, N-[4-[2-(3,4-dichlorophenyl)ethyl]phenyl]-3-methoxy, mp 162°–163° C.

EXAMPLE 148

Benzo[b]thiophene-2-carboxamide, N-[4-[2-[3,5-bis(trifluoromethyl)phenyl]ethyl]phenyl]-3-hydroxy, mp 203°–205° C.

VIII. Preparation of Compounds of Formula I Wherein Q is $I_5$

The starting material for preparing a compound of Formula I, wherein Q is $I_5$ may be prepared as exemplified in the following example.

EXAMPLE 149

4H-Furo[3,2-c][1]benzopyran-2,3-dione (see Scheme VII, Formula $XII_5$ Wherein $R_1$ is hydrogen)

To a stirred solution of 4-[(trimethylsilyl)oxy]-2H-1-benzopyran (L. H. Hellberg, and A. Zuarez, *Tetrahedron Letters*, 40, 3553 (1974)) (205.8 g, 0.917 mole) in anhydrous ether (600 ml) oxalyl chloride (58.2 g, 0.458 mole) is added dropwise over a period of 40 minutes at room temperature under nitrogen. The suspension is stirred at room temperature for 18 hours and then diluted with isopropyl ether (~300 ml). The precipitate is collected by filtration and washed with isopropyl ether to give 80.2 g (86%) of orange-red solid, mp 146°–8° C. Recrystallization from tetrahydrofuranisopropyl ether gives an analytical sample, mp 146°–148° C.

Preparation of compounds of Formula I wherein Q is $I_5$ are exemplified by the following examples.

EXAMPLE 150

N-[4-[2-(3,4-Dihydroxyphenyl)ethyl]phenyl]-4-hydroxy-60-oxo-2H-1-benzopyran-3-acetamide (See Scheme I, Formula I wherein Q is $I_5$ wherein $R_1$ is hydrogen; y is 2, $R_5$ is hydrogen and $R_6$ is 4-[2-(3,4-dihydroxyphenyl)ethyl]

Prepared by the method of Scheme I, from from 4H-furo[3,2-c][1]benzopyran-2,3-dione as prepared in Example 149 above (5.6 g, 0.0275 mole) and 4-(3,4-dihydroxyphenethyl)aniline (5.73 g, 0.025 mole) in tetrahydrofuran (300 ml). The solvent is removed under reduced pressure on a rotary evaporatory below 30° C. and the resulting solid is chloroform (400 ml) is stirred mechanically at reflux for 40 minutes. The precipitate is removed by filtration and washed with chloroform to give 10.2 g of a solid, which is dissolved in tetrahydrofuran and chromatographed on silica gel (200 g). Elution of the column with tetrahydrofuran gives 9.4 g of a solid. Recrystallization from ethanol yields 6.8 g (63%) of a yellow crystalline solid, mp 161°–3° C.

EXAMPLE 151

N-(4-Decylphenyl)-4-hydroxy-α-oxo-2H-1-benzopyran-3-acetamide (See Scheme I, Formula I, Wherein Q is $I_5$, Wherein $R_1$ is hydrogen; y is 2; $R_5$ is hydrogen; and $R_6$ is 4-[2-decylphenyl)ethyl]

A mixture of 4H-furo[3,2-c][1]benzopyran-2,3-dione as prepared in 149 above (5.6 g, 0.0275 mole) and 4-decylaniline (5.85 g, 0.025 mole) in dry tetrahydrofuran (250 ml) is stirred at room temperature under nitrogen for 18 hours in the dark. The solvent is removed under reduced pressure on a rotary evaporator below 40° C. and the resulting solid is recrystallized twice from methylene chloride-acetonitrile to give 9.54 g (87.5%) of a light-yellow crystalline solid, mp 119°–120° C.

In a manner analogous to Examples 149 or 150 above, using approriate starting materials the following compounds of Formula I wherein Q is $I_5$ were prepared.

EXAMPLE 152

2H-1-[Benzopyran-3-acetamide, N-[4-[2-(3,4-dimethoxyphenyl)ethyl]phenyl]-4-hydroxy-α-oxo, mp 170°–171° C.

EXAMPLE 153

2H-1-Benzopyran-3-acetamide, N-[4-[2-(4-chlorophenyl)ethyl]phenyl]-4-hydroxy-α-oxo, mp 146°–148° C.

EXAMPLE 154

2H-1-Benzopyran-3-acetamide, N-[4-[2-(4-hydroxy-3-methoxyphenyl)ethyl]phenyl]-4-hydroxy-α-oxo

EXAMPLE 155

2H-1-Benzopyran-3-acetamide, N-[4-[2-(3,4-dichlorophenyl)ethyl]phenyl]-4-hydroxy-α-oxo, mp 159°–160° C.

IX. Preparation of Compounds of Formula I Wherein Q is $I_6$

The preparation for a compound of Formula I wherein Q is $I_6$ is exemplified in the immediately following examples.

EXAMPLE 156

2H-Furo[3,2-b]indole-2-acetamide, N-[4-[2-(3,4-dimethoxyphenyl)ethyl]phenyl]-3,4-dihydro-7-methoxy-α,3-dioxo-4-phenyl (See Scheme I, Formula I Wherein Q is $I_6$ Wherein $R_1$ is 7-methoxy; b is one; $R_2$ is hydrogen; $R_5$ is hydrogen; y is 2; $R_6$ is 4-[2-(3,4-dimethoxyphenyl)ethyl])

A mixture of 2.4 g (0.050 mole) of 50% sodium hydride mineral oil suspension is 150 ml of N,N-dimethylformamide under a nitrogen atmosphere was stirred and cooled in ice. To the mixture was added over 30 minutes, 13.4 g (0.048 mole) of 7-methoxy-4-phenyl-2H-furo[3,2-b]indole-3(4H)-one. After stirring for an additional one hour, 18.9 g (0.053 mole) of [4-[2-(3,4-dimethoxyphenyl)ethyl]phenylamino]oxoacetic acid ehtyl ester was added, and the ice bath was removed.

The mixture was stirred for 48 hours, added to 1.0 kg ice/water, and acidified with 3N hydrochloric acid. The precipitated solid was filtered, washed with water, and recrystallized from N,N-diethylformamide/water to yield 18.6 g (66% yield) of amide product, mp 261°–263° C.

EXAMPLE 157

2H-Furo[3,2-b]indole-2-carboxamide, N-[4-[2-(4-methoxyphenyl)ethyl]phenyl]-3,4-dihydro-4-methyl-3-oxo (see Scheme I, Formula I Wherein Q is $I_6$ Wherein b is zero, $R_2$ is methyl; y is 1; $R_5$ is hydrogen; and $R_6$ is 4[2-(4-methoxyphenyl)ethyl])

Prepared by the procedure described in Example 156 above from 5.0 g (0.027 mole) of 4-methyl-2Hfuro[3,2-b]indole-3(4H)-one, except that [4-[2(4-methoxyphenyl)ethyl]phenyl-N,N-diphenyl urea (12.4 g, 0.029 mole) was employed as the acylating agent rather than the mixed ester-amide used in the Example 156. Recrystallization of the final product from 2-mehoxyethanol yielded 5.0 g (43% yield) of the amide product, mp 224°–226° C.

EXAMPLE 158

2H-Furo[3,2-b]indole-2-carboxamide, N-[4-[2-(3,4-Dimethoxyphenyl)ethyl]phenyl-3,4P-dihydro-7-methoxy-3-oxo-4-phenyl (See Scheme I, Formula I Wherein Q is $I_6$ Wherein $R_1$ is 7-methoxy, $R_2$ is phenyl, $R_5$ is hydrogen; and $R_6$ is 4-[2-(3,4-dimethoxyphenyl)ethyl])

A mixture of 16.6 g (23.0 ml, 0.16 mole) of diisopropylamine in 150 ml of tetrahydrofuran under a nitrogen atmosphere was cooled to 0° to −10° C. in an ice-/sodium chloride cooling bath. The mixture was stirred and treated over 20 minutes with a solution of 63 ml (0.16 mole) of n-butyl lithium (2.6M in n-hexane) at a rate that allowed the reaction mixture temperature to remain at <0° C. The mixture was stirred for an additional 20 minutes, and then a solution of 20.0 g (0.078 mole) of 4-[2-(3,4-dimethoxyphenyl)ethyl]benzenamine in 150 ml of tetrahydrofuran was added over 30 minutes. After stirring for an additional 40 minutes, a solution of 18.0 g (0.053 mole) of 3-hydroxy-7-methoxy-4-phenyl-4H-furo[3,2-b]indole-2-carboxylic acid methyl ester (Preparation described in U.S. patent application Ser. No. 369,448 now issued as U.S. Pat. No. 4,503,236) in 150 ml of 1,3-dimethyl-2-imidazolidinone was added over 45 minutes. The mixture was stirred with the cooling bath in place for an additional 45 minutes, then for 18 hours with the bath removed. The reaction mixture was added to 2.5 kg of ice/water containing 50 ml of concentrated hydrochloric acid. After stirring for two hours, the precipitated product was filtered, washed with water, and recrystallized from 2-methoxyethanol/water to yield 10.6 g (35% yield) of the amide product, mp 180° C. dec.

The next two examples show ether cleavage to prepare compounds of Formula I wherein $R_6$ included hydroxy substituents.

EXAMPLE 159

4H-Furo[3,2-b]indole-2-carboxamide, N-[4-[2-(3,4-Dihydroxyphenyl)ethyl]phenyl]-3-hydroxy-4-methyl (See Formula I Wherein Q is $I_6$, Wherein b is zero, $R_2$ is mehtyl; $R_5$ is hydrogen; y is 1; $R_6$ is 4-[2-(3,4-dihydroxyphenyl)ethyl])

A mixture of 10.6 g (0.034 mole) of boron tribromide dimethyl sulfide complex in 125 ml of 1,2-dichloroethane was treated, under a nitrogen atmosphere, with 1.9 g (0.004 mole) of N-[4-[2-(3,4-dimethoxyphenyl)ehtyl]phenyl]-3-hydroxy-4-methyl-4H-furo[3,2-b]indole-2-carboxamide. The mixture was stirred at reflux for 18 hours, cooled in ice, and treated with 150 g ice/water. After mixture was stirred at reflux for 18 hours, cooled in ice, and treated with 150 g ice/water. After stirring for several hours, the insoluble material was filtered and washed with water. Recrystallization from acetonitrile/N,N-dimethylformamide/water yielded 1.1 g (59% yield) of the catechol product, mp 200° C. dec.

EXAMPLE 160

2H-Furo[3,2-b]indole-2-carboxamide, N-[4-[2-(4-hydroxyphenyl)ethyl]phenyl-3,4-dihydro-4-methyl-3-oxo (See Formula I Wherein Q is $I_6$, Wherein b is zero, $R_2$ is methyl, y is 1, $R_5$ is hydrogen; $R_6$ is 4-[2-(4-hydroxyphenyl)ethyl])

A mixture of 4.0 g (0.009 mole) of 3,4dihydro-N-[4-[2-(4-methoxyphenyl)ethyl]phenyl]-4-methyl-3-oxo-2H-furo[3,2-b]indole-2-carboxamide in 125 ml of dichloromethane under a nitrogen atmosphere was cooled to −78° C. To the mixture was added 39 ml (0.039 mole) of 1.0M solution of boron tribromide in dichloromethane. The cooling bath was removed, and the mixture was stirred for 18 hours. The mixture was recooled in an ice bath and treated with 500 g ice/water and 500 ml ethyl acetate. The insoluble material was filtered and reserved, and the filtrate organic layer was separated, dried (sodium sulfate), and evaporated. The evaporation residue was combined with the original insoluble material and recrystallized from acetonitrile to yield 1.8 g (47% yield) of the phenol product, mp 261°–262° C.

In an analogous manner as the above Examples 151–160 for the respective procedures using appropriate starting materials the following additional compounds are prepared.

EXAMPLE 161

4H-Furo[3,2-b]indole-2-carboxamide, N-[4-[2-(3,4-dimethoxyphenyl)ethyl]phenyl]-3-hydroxy-4-methyl, mp 200°–201° C.

EXAMPLE 162

2H-Furo[3,2-b]indole-2-carboxamide, N-[4-[2-(3,4-dihydroxyphenyl)ehyl]phenyl]-3,4-dihydro-7-hydroxy-4-phenyl-α,3-dioxo, 1 DMF, mp 265° C. dec

EXAMPLE 163

2H-Furo[3,2-b]indole-2-carboxamide, N-[4-[2-(3,4-dihydroxyphenyl)ethyl]phenyl]-3,4-dihydro-7-hydroxy-3-oxo-4-phenyl, 225° C. dec

EXAMPLE 164

2H-Furo[3,2-b]indole-2-acetamide, N-[4-[2-(3,4-dimethoxyphenyl)ethyl]phenyl]-3,4-dihydro-4-methyl-α,3-dioxo, 0.4H$_2$O, mp 250°–254° C.

EXAMPLE 165

2H-Furo[3,2-b]indole-2-acetamide, N-[4-[2-(3,4-dihdroxyphenyl)ethyl]phenyl]-3,4-dihydro-4-methyl-α,3-dioxo, 0.5 DMF, mp 257°–8° C.

EXAMPLE 166

2H-Furo[3,2-b]indole-2-carboxamide, N-[4-[2-(3,4-dihydroxyphenyl)ethyl]phenyl]-3,4-dihydro-3-oxo-4-phenyl, 0.5H$_2$O, 192° C. dec X. Preparation of Compounds of Formula I Wherein Q is $I_7$ Intermediate ethers and compounds of Formula I of the present invention wherein Q is $I_7$ prepared by the method of cleaving the ethers are shown in Scheme IX and exemplified hereafter.

EXAMPLE 167

1H-Indole-2-carboxamide, N-[4-[2-(3,4-dimethoxyphenyl)ethyl]phenyl]-3-methoxy-1-phenyl (See Scheme IX, Formula XI$_7$ Wherein b is zero, $R_2$ is methyl, $R_3$ is methyl; y is one, X is hydrogen; $R_5$ is hydrogen; $R_6$ is 4-[2-(3,4-dimethoxyphenyl)ethyl])

A mixture of 8.0 g (0.030 mole) of 3-methoxy-1-phenyl-1H-indole-2-carboxylic acid and 7.8 g (0.030 mole) of 4-[2-(3,4-dimethoxyphenyl)ethyl]benzenamine in 125 ml of dichloromethane was cooled in ice and treated with 8.6 ml (6.2 g, 0.030 mole) of triethylamine, followed by 7.7 g (0.030 mole) of N,N-bis[2-oxo-3-oxazolidinyl]phosphorodiamidic chloride (Chemical Dynamics Corp., South Plainfield, NJ). The ice bath was removed, and the mixture was stirred for 48 hours, then treated with 250 g of ice/water. The mixture was acidified with 4.0N hydrochloric acid, and the organic layer was separated. The aqueous layer was washed with fresh dichloromethane (2×100 ml) and the combined organic layers were washed with water (1×125 ml), 5% aqueous sodium bicarbonate (2×125 ml), and water (1×125 ml) again. The organic layer was dried (sodium sulfate) and evaporated. Recrystallization of the residue from methanol/N,N-dimethylformamide/water yielded 9.7 g (64% yield) of the amide product, mp 129°–131° C.

EXAMPLE 168

1H-Indole-2-carboxamide,

N-[4-[2-(3,4-Dimethoxyphenyl)ethyl]phenyl]-3-methoxy-1-methyl (See Scheme IX, Formula XI$_7$ Wherein b is zero, R$_2$ is methyl, R$_3$ is methyl; X is hydrogen, and R$_6$ is 4-[2-(3,4-dimethoxyphenyl)ethyl])

A mixture of 10.7 g (0.052 mole) of 3-methoxy-1-methyl-1H-indole-2-carboxylic acid and 14.0 g (0.056 mole) of N-ethoxycarbonyl-2-ethoxy-1,2-dihydroquinoline ("EEDQ") in 185 ml of toluene was stirred at room temperature for two hours. To the mixture was added 14.1 g (0.055 mole) of 4-[2-(3,4-dimethoxyphenyl)ethyl]benzenamine, and stirring was continued for 72 hours. The mixture was refrigerated for several hours, and the insoluble material was filtered and washed with water. Recrystallization from methanol yielded 9.7 g (42% yield) of the amide product, mp 130°–131° C.

EXAMPLE 169

1H-Indole-2-carboxamide,

N-[4-[2-(3,4-Dimethoxyphenyl)ethyl]phenyl]-N-ethyl-3-methoxy-1-methyl (See Scheme IX, Formula XI$_7$ Wherein b is zero, R$_2$ is methyl, R$_3$ is methyl, X is ethyl; R$_5$ is hydrogen; y is 1; R$_6$ is 4-[2-(3,4-dimethoxyphenyl)-ethyl])

A mixture of 2.7 g (0.048 mole) of powdered potassium hydroxide in 23 ml of dimethyl sulfoxide was stirred for five minutes and treated with 5.3 g (0.012 mole) of N-[4-[2-(3,4-dimethoxyphenyl)ethyl]phenyl]-3-methoxy-1-methyl-1H-indole-2-carboxamide, followed by 2.0 ml (3.8 g, 0.024 mole) of iodoethane. The mixture was stirred at room temperature for 20 hours, poured into 300 ml water, and extracted with dichloromethane (3×300 ml). The combined organic layers were washed with water (1×200 ml), dried (sodium sulfate), and evaporated. Recrystallization of the residue from methanol yielded 4.3 g (76% yield) of the N-ethylamide product, mp 133°–134° C.

In a manner analogous to Examples 167–169 using appropriate starting materials the following additional intermediates are prepared.

EXAMPLE 170

1H-Indole-2-carboxamide, N-[4-[2-(3,4-dimethoxyphenyl)ethyl]phenyl]-N-ethyl-3,5-dimethoxy-1-phenyl (oil)

EXAMPLE 171

1H-Indole-2-carboxamide, N-[4-[2-(3,4-dimethoxyphenyl)ethyl]phenyl]-3-methoxy, mp 187°–190° C.

EXAMPLE 172

1H-Indole-2-carboxamide, N-[4-[2-(3,4-dimethoxyphenyl)ethyl]phenyl]-5-methoxy-1-phenyl-3-(phenylmethoxy), mp 120.5°–122.5° C.

EXAMPLE 173

1H-Indole-2-carboxamide, N-[4-[2-(3,4-dimethoxyphenyl)ethyl]phenyl]-3,5-dimethoxy-1-phenyl, mp 147°–149° C.

EXAMPLE 174

1H-Indole-2-carboxamide, N-[4-[2-(3,4-dimethoxyphenyl)ethyl]phenyl]-3-methoxy-1-(phenylmethyl), mp 131°–133° C.

EXAMPLE 175

1H-Indole-2-acetamide, N-[4-[2-(3,4-dimethoxyphenyl)ethyl]phenyl]-3-hydroxy-5,6-dimethyl-α-oxo (See Scheme IX, Formula I Wherein Q is I$_7$ Wherein b is two, R$_1$ is 5,6-dimethyl; R$_2$ is hydrogen; X is hydrogen; y is 2; R$_5$ is hydrogen, R$_6$ is 4-[2-(3,4-dimethoxyphenyl)ethyl])

A mixture of 12.5 g (0.054 mole) of 3-hydroxy-5,6-dimethyl-α-oxo-1H-indole-2-acetic acid (Preparation described in U.S. Pat. No. 4,260,544) and 14.4 g (0.058 mole) of N-ethoxy-carbonyl-2-ethoxy-1,2-dihydroquinoline ("EEDQ") in 1500 ml of toluene plus 200 ml of tetrahydrofuran was stirred at room temperature for three hours. To the mixture was added 14.5 g (0.056 mole) of 4-[2-(3,4-dimethoxyphenyl)ethyl]benzenamine, and stirring was continued for 64 hours. The insoluble material was filtered and reserved, and the filtrate was evaporated. The residue was combined with the original insoluble material and recrystallized from dichloromethane/hexane to yield 4.0 g (16% yield) of the amide product, mp 233°–236° C.

Ether cleavage for dimethyl ethers of compounds having the Formula I wherein Q is I$_7$ is exemplified as follows.

EXAMPLE 176

1H-Indole-2-carboxamide, N-[4-[2-(3,4-Dihydroxyphenyl)ethyl]phenyl]-3-hydroxy-1-methyl (See Scheme IX, Formula I Wherein Q is I$_7$, Wherein b is zero; y is 1; R$_2$ is methyl; X is hydrogen; R$_5$ is hydrogen; R$_3$ is hydrogen; R$_6$ is 4-[2-(3,4-dihydroxyphenyl)ethyl])

A mixture of 3.3 g (0.0074 mole) of N-[4-[2-(3,4-dimethoxyphenyl)ethyl]phenyl]-3-methoxy-1-methyl-1H-indole-2-carboxamide in 115 ml of dichloromethane under a nitrogen atmosphere was stirred and cooled to −78° C. To the mixture was added 31.3 ml (0.031 mole) of 1.0M boron tribromide in dichloromethane. The mixture was stirred for 90 minutes at −78° C., and then for 24 hours with the cooling bath removed. The mixture was recooled in an ice bath, treated with 300 g ice/water and 300 ml of ethyl acetate. After stirring for several hours, the layers were separated and the aqueous layer was extracted with fresh ethyl acetate (2×300 ml). The combined organic layers were washed with water (1×300 ml), dried (sodium sulfate), and evaporated. Recrystallization of the residue from methanol/water yielded 1.8 g, 60% yield) of the catechol product, mp 194°–197° C. dec.

EXAMPLE 177

1H-Indole-2-acetamide, N-[4-[2-(3,4-dihydroxyphenyl)ethyl]phenyl]-3-hydroxy-5,6-dimethyl-α-oxo (See Scheme IX) Formula I Wherein Q is $I_7$ Wherein $R_1$ is 5,6-dimethyl; b is two; y is two; $R_5$ is hydrogen; $R_3$ is hydrogen; $R_6$ is 4-[2-(3,4-dihydroxyphenyl)ethyl])

A mixture of 9.7 g (0.031 mole) of boron tribromide dimethylsulfide complex in 150 ml of 1,2-dichloroethane under a nitrogen atmosphere was treated with 3.0 g (0.0064 mole) of N-[4-[2-(3,4-dimethoxyphenyl)ethyl]phenyl]-3-hydroxy-5,6-dimethyl-α-oxo-1H-indole-2-acetamide. The mixture was stirred at reflux for 18 hours, cooled, and treated with 600 g of ice/water. After stirring for several hours, the insoluble material was filtered, washed with water, and refiltered. Recrystallization from acetonitrile/N,N-dimethylformamide/water yielded 0.31 g (11% yield) of catechol product, mp 239°–241° C.

In a manner analgous to the respective Examples 175–176 using appropriate starting materials the following compounds of Formula I, Wherein Q is $I_7$ are prepared.

EXAMPLE 178

1H-Indole-2-carboxamide, N-[4-[2-(3,4-dihydroxyphenyl)ethyl]phenyl]-3-hydroxy-, mp 236°–238° C.

EXAMPLE 179

1H-Indole-2-acetamide, N-(4-decylphenyl)-3-hydroxy-5,6-dimethyl-α-oxo, mp 210°–211° C.

The usefulness of the compounds of the present invention as inhibitors of lipoxygenase enzyme or antagonists of leukotriene or other related biochemical actions is demonstrated by their effectiveness in various standard pharmacological test procedures. A description of each procedure follows.

Human Leukocyte Lipoxygenase Assay (LDA-H)

Whole blood is collected from normal volunteers and spun in a refrigerated centrifuge for four minutes at 1°–6° C. at 3800 g. The buffy coat is manually separated and washed twice with chilled 0.83% $NH_4Cl$ and centrifuged at 1000 RPM for ten minutes at 4° C. The white cell is suspended in culture media-EMEM supplemented with 6% Agamma human serum, tricine buffer, and neomycin and recentrifuged at 1000 g to yield a pellet containing the leukocytes used for the preparation of the acetone pentane powder.

The acetone-pentane powder is prepared utilizing a modification of the procedure reported for human platelet lipoxygenase. See Siegel, et al, Arachidonate Metabolism via Lipoxygenase and 12-L-hydroperoxy-5 Eicosatetraenoic Acid Peroxidase Sensitive to Antiinflammatory Drugs, *Proc. Natl. Acad. Sci.*, USA 77: 308, 1980 and D. P. Wallach and V. R. Brown, A Novel Preparation of Human Platlet Lipoxygenase, *Biochem. Biophys. Acta.* 663: 361, 1981. Buffy coat prepared above is resuspended in 5–7 volumes of cold 0.1M Tris buffer, pH 7.4 containing 0.154M NaCl. The suspension is centrifuged at 13,300 g for ten minutes at 4° C. The resultant pellet is retained, resuspended in five volumes of cold acetone, recentrifuged at 13,300 g and resuspended in five volumes of cold pentane. The pentane suspension is centrifuged for ten minutes at 13,300 g to give a pellet which is dried in the cold under vacuum with periodic pulverization. The dry powder is stable for several weeks when stored at −80° C.

Enzyme stock solution is prepared in the following manner. About 15 mg of the acetone-pentane powder is suspended in 4 ml of cold tris buffer (0.1M, pH 7.4), allowed to stand for five minutes, and homogenized thoroughly. The homogenate is sonicated three times for 15 seconds each time, diluted to 7 ml with cold tris buffer (0.1M, pH 7.4), and centrifuged at 4° C. for 60 minutes at 13,300 g. the supernatent is retained and diluted to a total of 10 ml with cold tris buffer (0.1M, pH 7.4) to give the stock enzyme solution. Additional dilutions of 2–50 fold are done as necessary to locate optimal enzyme reaction rate in the assay described below.

Substrate solution is prepared at 100 μM or 1.0 μM concentrations of arachidonic acid or linoleic acid in 0.1M tris buffer, pH 9.0 containing 20% ethanol.

The enzyme reaction is followed spectrophotometrically by the appearance of a conjugated diene product at 234 nm. The reaction is monitored at 24° C. using a Gilford Model 2600 spectrophotometer. Each assay had a total volume of 1.0 ml and contained substrate, tris buffer (0.1M, pH 9.0), 2% ethanol, and sufficient enzyme to give an easily measurable initial rate of reaction. The effects of inhibitors on the reaction are compared with control reactions run under indentical conditions. Routinely, each compounds of the present invention is incubated with the enzyme for five minutes prior to addition of substrate to initiate the reaction. Inhibition expressed as $IC_{50}$ as molar concentration of the compound required to reduce reaction rate to 50% control.

Binding of $^3$H-Leukotriene $D_4$ to Guinea Pig Lung Membranes (RBL)

Materials

[14,15-$^3$H]leukotriene $D_4$ ($^3$H-LTD$_4$) (25 Ci/mmol and 40 Ci/mmol) is purchased from New England Nuclear. Unlabeled LTC$_4$ is a gift of Ono Pharmaceuticals (Japan). LTC$_4$, LTD$_4$, and LTE$_4$ are purchased as methyl esters from Paesel GmbH (Frankfurt, W. Germany). Concentrations of the Paesel leukotrienes are calculated from their absorbance at 280 nm. Leukotriene esters are saponified overnight under $N_2$ in 3.3% potassium carbonate at room temperature. Tritiated leukotrienes are stored as received from New England Nuclear at −20° C. Ono LTC$_4$ (5 μg/ml) is stored at −60° C. in phosphate buffer pH 6.8. Saponified Paesel leukotrienes are stored at −60° C. in 3.3% potassium carbonate (pH 9.0–9.5). Aliquots of leukotrienes are taken from stock solutions immediately after thawing, after which the stock solutions are immediately refrozen. 2-Amino-2-(hydroxymethyl)-1,3-propanediol (Tris) is Sigma pH 7.7 pre-set crystals, and dimethylsulfoxide is Aldrich Gold Label.

Preparation of crude lung membranes

Two pairs of lungs (1.3 g) from freshly sacrificed 300 g male guinea pigs (older animals gave substantially lower binding) from Kuiper Rabbit Farm, Gary, IN are disrupted with a Polytron PT 10 (setting 4) for 30 seconds in 20 ml ice-cold 50 mM Tris adjusted with HCl to pH 7.7 at 25° C. (Tris buffer), filtered through a single layer of gauze to remove connective tissue, and centrifuged at 50,000 xg for ten min. The pellet is resuspended by homogenization with a Polytron in 20 ml Tris buffer, centrifuged at 50,000 xg for ten min., resuspended, incubated at 37° C. for 30 minutes, and centrifuged again. The final pellet is resuspended in Tris buffer and either used fresh or stored at −70° C.

Binding assay

All incubations are in triplicate for 60 minutes at 25° C. in 12×75 mm polystyrene tubes containing 1 ml Tris buffer with 20 mg original tissue wet weight of guinea pig lung nmembranes, 0.2 nM $^3$H-LTD$_4$ (6,000–11,000 cpm), 10 mM MgCl$_2$, and 1% dimethylsulfoxide Leukotrienes are diluted in Tris buffer. All other test compounds dissolved at 10 mM in dimethylsulfoxide on the same day as the experiment, and diluted in dimethylsulfoxide to 100× the final incubation concentration. Control incubations receive an equal volume (10 μl) of dimethylsulfoxide; the resulting concentration of dimethylsulfoxide had no effect on binding. $^3$H-LTD$_4$ is diluted to 2 nM in Tris buffer. The membrane suspension (20 mg/0.89 ml) contains sufficient MgCl$_2$ to give 10 mM final concentration in the incubation. For test compounds with IC$_{50}$ values less than 1 μM, the order of incubations is test compound (10 μl), $^3$H-LTD$_4$ (100 μl), and membranes (0.89 ml). For test compounds with IC$_{50}$ values greater than 1 than 1 μM and limited water solubility, the order of additions is test compound, membranes, and $^3$H-LTD$_4$. All additions are performed at 0° C. Immediately after the last addition, the incubation is initiated by agitating the rack of tubes on a vortex mixer and warming to 25° C. in a water bath. Tubes are vortexed at least once more during the incubation to ensure that the membranes remained suspended. Incubations are terminated after 60 minutes by filtering under reduced pressure through 25 mm Whatman GF/B filters followed by rapid washing three times with 4 ml of ice-cold Tris buffer. Filters are added to scintillation vials with 8 ml Formula 947 (New England Nuclear), left overnight, shaken, and the radioactivity counted in a scintillation counter (efficiency 40%). Nonspecific binding, defined as binding of $^3$H-LTD$_4$ in the presence of 100 nM LTC$_4$, is 300–500 cpm for all lots of $^3$H-LTD$_4$. Binding to the filters in the absence of tissue is about 100 cpm, and is not affected by unlabeled LTC$_4$. Specific binding, defined as total binding minus nonspecific binding, varied considerably from lot to lot of $^3$H-LTD$_4$. Specific $^3$H-LTD$_4$ binding ranged from 1500 to 3000 cpm, and is greater than 80% of total binding for the better lots of $^3$H-LTD$_4$.

To Evaluate the Effect of Each Compounds as a 5-Lipoxygenase Inhibitor in Comparison to Standard Reference Agents in Human Leukocytes (5LOA1)

The purpose of this assay is to evaluate the activity of each compound as an inhibitor of human leukocyte 5-lipoxygenase.

Arachidonic acid and calcium ionophore A23187 are obtained from Sigma (St. Louis, MO). Silica gel plates, GF are obtained from Analtech (Newark, DE). Arachidonic acid, (1-$^{14}$C) and 5-HETE ($^3$H), 5 (S)-hydroxy-6-trans,8,11,14-cis eicosatetraenoic acid, are obtained from New England Nuclear (Boston, MA). Six percent Dextran-70 in 0.9% NaCl is obtained from Cutter Labs (Berkeley, CA).

Preparation of Leukocytes

Fresh blood from normal adult men who had not received any drugs for at least the previous five days is obtained by the Community Research Clinic (WL/PD) using venipuncture and collected into heparinized vacuotainer tubes. To every 100 ml of pooled blood is added 25 ml of dextran solution (6% dextran −70 in 0.9% sodium chloride containing 3% dextrose) and this is mixed gently in a plastic cylinder. The mixture is left to stand at room temperature for at least 90 minutes. The upper layer which is rich in leukocytes and platelets is then carefully decanted into 50 ml plastic tubes and centrifuged at about 100×g for eight minutes in an IEC centrifuge and rotor number 269 (about 600 rpm). The supernatant fluid is discarded and the pellet is resuspended in 10 ml of 0.87% ammonium chloride for exactly two minutes. This procedure is to lyse completely contaminating red blood cells. Leukocytes are then separated by centrifugation for ten minutes. The pellet is washed three times by suspension in 20 ml PBS (sodium chloride, 7.1 g; Na$_2$HPO$_4$, 1.15 g; KH$_2$PO$_4$, 0.2 g, and KCl, 0.2 g/L) and centrifuged as before. The final pellet is suspended in PBS containing 0.87 mM CaCl$_2$. Viability of the cells is then checked using trypan blue exclusion method and is found to be over 90%.

5-Lipoxygenase Enzyme Assay

Leukocyte cells in suspension (0.98 ml) are incubated with or without test compounds for five minutes at 37° C. in a shaking water bath. At this time a 17 μl mixture is prepared per 1 ml of cell suspension: 100 mM arachidonic acid, 1 μl, 0.05 μCi $^{14}$C-arachidonic acid in 5 μl; 1 mM calcium ionophore A23187, 10 μl (1). This mixture is added and the incubation continued for five minutes. The reaction is stopped by adding four volumes of absolute ethanol and the mixture is kept in ice for 30 minutes. The flocculated precipitate is separated by centrifugation at about 37,000×g for 20 minutes (Beckman Instruments rotor number 40). The alcohol extract is taken to dryness under a stream of nitrogen and the residue is dissolved in 100–200 μl absolute ethanol. At the time any turbidity is removed by centrifugation. An aliquot (25–50 μl) is applied onto 20×20 cm silica gel TLC plate and developed using the following solvent system: diethyl ether, petroleum ether (2040° C.), acetic acid (50:50:1 v/v). Zones of 1 cm apart are scraped from the TLC plate and transferred to minivials. Methanol (0.5 ml) is added to dissolve the radioactivity adsorbed to the silica gel and scintillation fluid (H. P., Beckman), 5 ml is then added and vials are counted in a liquid scintillation counter. A sample of $^3$H-5-HETE is applied and used for the identification of the formed 5-HETE.

Total radioactivity in the test as well as the control samples are normalized and the amount of 5-HETE present is calculated accordingly.

IC$_{50}$ values are defined as the concentrations of test agents which caused a 50% inhibition of the formation of 5-HETE as compared to control and are determined by inspection of the concentration-response curves.

5-Lipoxygenase Assay Using Isolated Human Leukocytes (5LOA2)

The formation of 5-HETE in human leukocytes is considered a measure of 5-lipoxygenase activity. The protocol is described in the following.

Fresh heparinized or EDTA treated human blood is mixed with 6% dextran-3% dextrose in isotonic saline in the ratio 0.25 ml dextran solution per 1.0 ml blood. After mixing the blood is allowed to sit at room temperature for about 90 minutes while the RBC's settle. During this period, the plasma is removed with a plastic pepette to nalgens tubes.

The plasma is centrifuged at 800 rpm (125 kg) on the Beckman Td-b refrigerated centrifuge to remove the platelets (which remain in the supernatant). The pellet, consisting of leukocytes and erythrocytes, is treated with 10 ml 0.87% ammonium chloride at room temperature for four minutes, lysing the red cells. At the end of four minutes the cells are diluted with a 2x volume of phosphate buffered saline, pH 7.4, and centrifuged for ten minutes. The cells are washed three times with the phosphate buffered saline. Any of the pelleted cell matter which is not easily resuspended is discarded during the washings—the material contains platelets (12-lipoxygenase activity)

After washing, the cells are resuspended in phosphate buffered saline containing 1.0 mM calcium and 0.5 mM magnesium. After counting the cells are diluted to 1.5–2.0×10$^7$ leukocytes per milliliter.

To each polypropylene reaction tube is added 0.48 ml leukocytes in Ca-Mg phosphate buffered saline, pH 7.4; 1–5 μl test compound dissolved in DMSO and buffer; or DMSO for control tubes.

The tubes preincubate at 37° C. for five minutes.

The reaction is started by adding 20 μl of the following, 0.5 μl 20 mM arachidonic acid—final concentration=20 μm; 1 μl 5 mM calcium ionophore A23187—final concentration=10 μm; and 18.5 μl buffer.

The reaction proceeds for five minutes, then is stopped by adding 0.5 ml 0.5 mM ice cold Tris buffer, pH 8.0. The tubes are chilled on ice for ten minutes and then extracted three times with a total of 3.5 ml ethyl acetate (3.0 ml removed).

The tubes can be stored at this point. For extended storage, the tubes should be filled with nitrogen.

The ethyl acetate is evaporated with a Sorvall Speed-Vac. The residue is dissolved in ethanol. The tubes can also be stored at this point at −20° C. under nitrogen.

A portion of the ethanol solution is injected into the HPLC system for 5-HETE quantitation.

The HPLC system consists of Hewlett-Packard 1040A UV spectrophotometry system with an HP85 computer. Injections are made automatically with a Waters WISP 710B. The pump is a Spectra Physics SP8700. Peaks are measured with a Hewlett Packard 3390A integrator. An RP C-18 column is used. The solvent system is isocratic; the solvent is 70% methanol and 30% 0.01M sodium acetate, pH 5.7, pumped at 1.0 ml/min. The flow is monitored at 235 nm for 5-HETE quantitation. Using a 15 cm Alltech Nucleosil C-18 5 μM column provides for a sample turnaround time of about 16 minutes.

IC$_{50}$ is calculated as the amount of test agent that causes 50% inhibition of the formation of 5-HETE relative to the control.

The above defined values for each of tested compounds of the present invention having the noted Q groups is as found in the following TABLES.

TABLE 1

| | Q is I$_1$ Concentration (M) | % Inhibition |
|---|---|---|
| Example 18 | | |
| RBL | 7.19 E −5 | 50.0 IC |
| 5LOA | 1.35 E −5 | 50.0 IC |
| Example 16 | | |
| RBL | 1.28 E −5 | 50.0 IC |
| 5LOA | 1.77 E −5 | 50.0 IC |
| LDAH | 5.10 E −5 | 50.0 IC |
| Example 41 | | |
| RBL | 1.26 E −5 | 50.0 IC |
| LDAH | 4.50 E −5 | 50.0 IC |
| 5LOA | 7.00 E −6 | 50.0 IC |
| Example 40 | | |
| RBL | 5.60 E −5 | 50.0 IC |
| LDAH | 8.20 E −5 | 50.0 IC |
| Example 44 | | |
| RBL | 3.02 E −6 | 50.0 IC |
| 5LOA | 4.00 E −5 | 30.0 |
| | 2.00 E −5 | +5.8 |
| | 1.00 E −5 | +19.6 |
| LDAH | 2.50 E −5 | 0.0 |
| Example 45 | | |
| RBL | 9.44 E −6 | 50.0 IC |
| LDAH | 8.00 E −5 | 0.0 |
| Example 54 | | |
| RBL | 1.09 E −5 | 50.0 IC |
| 5LOA | 5.25 E −6 | 50.0 IC |
| LDAH | 3.50 E −6 | 50.0 IC |
| Example 46 | | |
| RBL | 2.15 E −5 | 50.0 IC |
| | 1.87 E −5 | 50.0 IC |
| 5LOA | 1.10 E −5 | 50.0 IC |
| LDAH | 1.10 E −5 | 50.0 IC |
| Example 39 | | |
| RBL | 2.48 E −5 | 50.0 IC |
| LDAH | 5.70 E −5 | 50.0 IC |
| Example 55 | | |
| RBL | 1.00 E −4 | 100.0 |
| | 1.00 E −6 | 5.0 |
| | 2.00 E −6 | 10.0 |
| | 5.00 E −6 | 13.0 |
| | 1.00 E −5 | 6.0 |
| | 2.00 E −5 | 12.0 |
| | 5.00 E −5 | 11.0 |
| | 1.00 E −4 | 21.0 |
| LDA | 6.80 E −5 | 50.0 IC |
| Example 47 | | |
| RBL | 1.11 E −5 | 50.0 IC |
| LDAH | 8.00 E −5 | 0.0 |
| Example 82 | | |
| RBL | 3.95 E −5 | 50.0 IC |
| LDAH | 8.00 E −5 | 0.0 |
| Example 12 | | |
| RBL | 1.00 E −5 | 0.0 |
| | 1.00 E −4 | 0.0 |
| LDAH | 3.40 E −6 | 50.0 IC |
| Example 35 | | |
| RBL | 4.23 E −5 | 50.0 IC |
| Example 30 | | |
| RBL | 2.26 E −5 | 50.0 IC |
| Example 28 | | |
| RBL | 5.00 E −5 | 50.0 IC |
| | 3.56 E −5 | 50.0 IC |
| Example 32 | | |
| RBL | 2.35 E −5 | 50.0 IC |
| Example 37 | | |
| RBL | 1.90 E −5 | 50.0 IC |
| LDAH | 8.00 E −5 | 0.0 |
| Example 38 | | |
| RBL | 6.68 E −6 | 50.0 IC |
| LDAH | 2.50 E −5 | 0.0 |
| Example 43 | | |
| RBL | 2.06 E −5 | 50.0 IC |
| LDAH | 8.00 E −5 | 0.0 |
| Example 27 | | |

TABLE 1-continued

| | Q is $I_1$ Concentration (M) | % Inhibition |
|---|---|---|
| RBL | 1.06 E −4 | 50.0 IC |
| 5LOA | 1.80 E −5 | 50.0 IC |
| RBL | 1.20 E −4 | 50.0 IC |
| Example 51 | | |
| RBL | 3.84 E −6 | 50.0 IC |
| 5LOA | 2.12 E −6 | 50.0 IC |
| LDAH | 2.50 E −5 | 0.0 |
| Example 21 | | |
| 5LOA | 7.00 E −7 | 50.0 IC |
| LDAH | 8.20 E −6 | 50.0 IC |
| Example 22 | | |
| LDAH | 1.30 E −5 | 50.0 IC |
| Example 38 | | |
| RBL | 2.65 E −5 | 50.0 IC |
| LDAH | 8.00 E −5 | 0.0 |
| Example 29 | | |
| RBL | 3.92 E −5 | 50.0 IC |
| Example 23 | | |
| LDAH | 2.50 E −5 | 0.0 |
| Example 14 | | |
| LDAH | 2.50 E −5 | 0.0 |
| Example 3 | | |
| LDAH | 2.50 E −5 | 0.0 |
| | 1.00 E −5 | 0.0 |
| Example 34 | | |
| RBL1 | 1.58 E −5 | 50.0 IC |
| Example 60 | | |
| 5LOA | 5.00 E −6 | 7.9 |
| | 1.00 E −5 | 25.2 |
| | 2.00 E −5 | 21.7 |
| LDAH | 2.50 E −5 | 50.0 IC |
| RBL | 1.21 E −5 | 50.0 IC |
| Example 48 | | |
| RBL | 6.48 E −6 | 50.0 IC |
| | 1.19 E −5 | 50.0 IC |
| | 2.00 E −5 | 50.0 IC |
| | 1.29 E −5 | 50.0 IC |
| 5LOA | 1.59 E −5 | 50.0 IC |
| | 1.91 E −5 | 50.0 IC |
| LDAH | 2.50 E −5 | 0.0 IC |
| Example 31 | | |
| RBL | 5.20 E −5 | 50.0 IC |
| Example 36 | | |
| RBL | 1.00 E −4 | 78.0 |
| | 2.00 E −6 | 6.0 |
| | 5.00 E −6 | 3.0 |
| | 1.00 E −5 | 7.0 |
| | 2.00 E −5 | 27.0 |
| | 5.00 E −5 | 59.0 |
| | 1.00 E −4 | 81.0 |
| | 3.15 E −5 | 80.0 |
| LDAH | 2.50 E −5 | 0.0 |
| Example 66 | | |
| RBL | 3.15 E −5 | 50.0 IC |
| Example 33 | | |
| RBL | 8.20 E −5 | 50.0 IC |
| LDAH | 2.50 E −5 | 50.0 IC |
| Example 6 | | |
| 5LOA | 2.00 E −5 | 50.6 IC |
| | 2.10 E −5 | 50.0 IC |
| Example 67 | | |
| RBL | 6.56 E −6 | 50.0 IC |
| Example 67 | | |
| RBL | 1.04 E −5 | 50.0 IC |
| 5LOA | 1.17 E −5 | 50.0 IC |
| Example 52 | | |
| LDAH | 6.00 E −5 | 50.0 IC |
| Example 49 | | |
| RBL | 1.49 E −4 | 50.0 IC |
| LDAH | 3.50 E −5 | 50.0 IC |
| Example 50 | | |
| LDAH | 8.00 E −5 | 0.0 |
| Example 59 | | |
| RBL | 7.29 E −6 | 50.0 IC |
| LDAH | 2.50 E −5 | 0.0 |
| Example 61 | | |
| RBL | 2.00 E −5 | 50.0 IC |
| | 2.05 E −5 | 50.0 IC |
| LDAH | 1.00 E −6 | IC |
| Example 9 | | |
| LDAH | 7.70 E −5 | 50.0 IC |
| Example 58 | | |
| RBL | 8.47 E −6 | 59.0 IC |
| LDAH | 8.00 E −5 | 0.0 |
| Example 11 | | |
| RBL | 3.64 E −6 | 50.0 IC |
| LDAH | 1.10 E −6 | 50.0 IC |
| Example 4 | | |
| LDAH | 4.50 E −5 | 50.0 IC |
| Example 68 | | |
| RBL | 4.99 E −6 | 50.0 IC |
| Example 69 | | |
| RBL | 2.04 E −5 | 50.0 IC |
| Example 53 | | |
| RBL | 3.54 E −6 | 50.0 IC |
| 5LOA | 3.80 E −6 | 50.0 IC |
| Example 70 | | |
| 5LOA | 5.00 E −6 | 50.0 IC |
| Example 71 | | |
| RBL | 7.46 E −6 | 50.0 IC |
| LDAH | 2.00 E −4 | 50.0 IC |
| Example 72 | | |
| RBL | 3.50 E −6 | 50.0 IC |
| LDAH | 2.60 E −6 | 50.0 IC |
| Example 62 | | |
| RBL | 1.00 E −5 | 50.0 IC |
| | 5.95 E −6 | 50.0 IC |
| | 4.98 E −6 | 50.0 IC |
| LDAH | 0.00 E 0 | 0.0 |
| Example 73 | | |
| RBL | 3.84 E −6 | 50.0 IC |
| 5LOA | 4.09 E −6 | 50.0 IC |
| | 8.20 E −6 | 50.0 IC |
| Example 64 | | |
| RBL | 6.11 E −6 | 50.0 IC |
| | 9.49 E −6 | 50.0 IC |
| | 2.82 E −6 | 50.0 IC |
| 5LOA | 1.19 E −5 | 50.0 IC |
| Example 63 | | |
| RBL | 4.42 E −6 | 50.0 IC |
| | 3.11 E −6 | 50.0 IC |
| Example 74 | | |
| RBL | 5.27 E −6 | 50.0 IC |
| 5LOA | 9.30 E −6 | 50.0 IC |
| Example 75 | | |
| RBL | 5.58 E −6 | 50.0 IC |
| Example 76 | | |
| RBL | 3.00 E −6 | 50.0 IC |
| 5LOA | 1.10 E −5 | 50.0 IC |
| Example 77 | | |
| RBL | 5.96 E −6 | 50.0 IC |
| Example 78 | | |
| RBL | 4.82 E −6 | 50.0 IC |
| 5LOA | 1.06 E −5 | 50.0 IC |
| Example 79 | | |
| RBL | 5.30 E −7 | 50.0 IC |
| | 4.13 E −7 | 50.0 IC |
| 5LOA | 9.20 E −6 | 50.0 IC |
| Example 80 | | |
| RBL | 1.27 E −5 | 50.0 IC |
| 5LOA | 1.01 E −5 | 50.0 IC |
| Example 81 | | |
| RBL | 1.01 E −5 | 50.0 IC |
| 5LOA2 | 8.40 E −6 | 50.0 IC |
| Example 8 | | |
| RBL | 4.21 E −6 | 50.0 IC |
| 5LOA2 | 5.00 E −6 | 50.0 IC |

TABLE 1-continued

| $Q$ is $I_1$ | |
|---|---|
| Concentration (M) | % Inhibition |
| 4.60 E −6 | 50.0 IC |

TABLE 2

| $Q$ is $I_2$ | |
|---|---|
| Concentration (M) | % Inhibition |
| *Example 83* | |
| 5LOA | |
| 5.00 E 0 | +1.6 |
| 2.00 E 0 | 9.2 |
| *Example 87* | |
| 5LOA | 4.00 E −7 | 50.0 IC |
| LDAH | 1.00 E 5 | 50.0 IC |

TABLE 3

| $Q$ is $I_3$ | |
|---|---|
| Concentration (M) | % Inhibition |
| *Example 101* | |
| 5LOA | 8.50 E −6 | 56.0 IC |
| LDAH | 2.50 E −5 | 0.0 |
| *Example 129* | |
| 5LOA | 5.00 E −7 | 50.0 IC |
| LDAH | 1.60 E −6 | 50.0 IC |
| *Example 117* | |
| LDAH | 2.50 E −5 | 0.0 |
| *Example 126* | |
| 5LOA | 3.55 E −6 | 50.0 IC |
|  | 2.17 E −6 | 50.0 IC |
| LDAH | 3.20 E −5 | 50.0 IC |
| *Example 121* | |
| 5LOA | 7.60 E −6 | 50.0 IC |
| LDAH | 1.60 E −6 | 50.0 IC |
| *Example 123* | |
| LDAH | 2.50 E −5 | 50.0 IC |
| *Example 124* | |
| 5LOA | 4.20 E −6 | 50.0 IC |
| LDAH | 6.50 E −6 | 50.0 IC |
| *Example 103* | |
| LDAH | 1.10 E −6 | 50.0 IC |
| *Example 122* | |
| 5LOA | 7.60 E −7 | 50.0 IC |
| LDAH | 2.30 E −6 | 50.0 IC |
| *Example 125* | |
| 5LOA | 4.01 E −6 | 50.0 IC |
| LDAH | 6.10 E −6 | 50.0 IC |
| *Example 115* | |
| LDAH | 8.00 E −5 | 0.0 |
| *Example 119* | |
| LDAH | 7.90 E −9 | 50.0 |
| *Example 113* | |
| 5LOA | 5.00 E −6 | 6.3 |
|  | 1.00 E −5 | 15.3 |
|  | 2.00 E −5 | 33.7 |
| *Example 110* | |
| 5LOA | 6.04 E −6 | 50.0 IC |
|  | 6.35 E −6 | 50.0 IC |

TABLE 4

| $Q$ is $L_4$ | |
|---|---|
| Concentration (M) | % Inhibition |
| *Example 131* | |
| RBL | 4.40 E −6 | 50.0 IC |
| LDAH | 7.00 E −6 | 0.0 IC |
| *Example 134* | |
| RBL | 6.88 E −5 | 50.0 IC |
| LDAH | 8.20 E −6 | 50.0 IC |
| *Example 135* | |
| RBL | 1.00 E −4 | 43.0 |

TABLE 4-continued

| $Q$ is $L_4$ | |
|---|---|
| Concentration (M) | % Inhibition |
| LDAH | 2.50 E −5 | 50.0 IC |
| *Example 136* | |
| RBL | 1.00 E −4 | 11.0 |
| 5LOA | 5.00 E −6 | +1.4 |
|  | 2.00 E −5 | +2.2 |
| *Example 137* | |
| RBL1 | 1.00 E −4 | 12.0 |
| *Example 139* | |
| RBL1 | 1.00 E −4 | 25.0 |
| *Example 138* | |
| RBL | 1.13 E −4 | 50.0 IC |
| LDAH | 3.30 E −5 | 50.0 IC |
| *Example 142* | |
| RBL | 6.10 E −5 | 50.0 IC |
| 5LOA | 6.00 E −6 | 50.0 IC |
| *Example 143* | |
| RBL | 1.21 E −5 | 50.0 IC |
| 5LOA | 5.22 E −6 | 50.0 IC |
| LDAH | 4.40 E −6 | 50.0 IC |
| *Example 144* | |
| RBL | 5.00 E −6 | 50.0 IC |
|  | 6.43 E −6 | 50.0 IC |
|  | 3.28 E −6 | 50.0 IC |
| 5LOA | 5.00 E −6 | 36.0 |
|  | 2.00 E −5 | 42.5 |
| *Example 145* | |
| RBL | 1.00 E −4 | 30.0 |
| 5LOA | 1.21 E −5 | 50.0 X1 |
| *Example 146* | |
| RBL | 1.02 E −6 | 50.0 IC |
| *Example 146* | |
| 5LOA | 3.96 E −6 | 50.0 IC |
| *Example 147* | |
| RBL | 1.00 E −4 | 3.0 |
| 5LOA | 5.00 E −6 | 5.5 |
|  | 2.00 E −5 | 13.8 |
| *Example 148* | |
| RBL | 1.00 E −4 | 50.0 IC |
| 5LOA | 5.00 E −6 | +7.3 |
|  | 2.00 E −5 | 19.0 |

TABLE 5

| $Q$ is $I_5$ | |
|---|---|
| Concentration (M) | % Inhibition |
| *Example 150* | |
| 5LOA | 1.80 E −6 | 50.0 IC |
| LDAH | 4.70 E −6 | 50.0 IC |
| *Example 152* | |
| 5LOA | 2.00 E −5 | 38.1 |
|  | 8.00 E −5 | 79.2 |
|  | 1.00 E −5 | 23.0 |
|  | 2.00 E −5 | 33.9 |
|  | 4.00 E −5 | 76.3 |
|  | 2.31 E −5 | 0.0 |
| LDAH | 5.70 E −7 | 50.0 IC |
| *Example 151* | |
| 5LOA | 1.00 E −5 | 13.9 |
|  | 4.00 E −5 | 18.0 |
| *Example 155* | |
| 5LOA | 5.00 E −6 | +7.6 |
|  | 1.00 E −5 | +6.5 |
|  | 2.00 E −5 | 10.1 |
|  | 1.00 E −5 | +5.2 |
|  | 4.00 E −5 | 2.3 |

TABLE 6

| $Q$ is $I_6$ | |
|---|---|
| Concentration (M) | % Inhibition |
| *Example 161* | |
| 5LOA | 9.00 E −6 | 50.0 IC |

TABLE 6-continued

Q is $I_6$

| | Concentration (M) | % Inhibition |
|---|---|---|
| Example 158 | | |
| 5LOA | 4.80 E −6 | 50.0 IC |
| LDAH | 0.00 E 0 | 0.0 |
| Example 159 | | |
| 5LOA | 1.18 E −6 | 50.0 IC |
| Example 163 | | |
| 5LOA | 5.00 E −7 | 50.0 IC |
| LDAH | 2.50 E −5 | 0.0 |
| Example 166 | | |
| LDAH | 2.70 E −5 | 50.0 IC |

TABLE 7

Q is $I_7$

| | Concentration (M) | % Inhibition |
|---|---|---|
| Example 175 | | |
| 5LOA | 2.00 E −6 | 8.0 |
| | 1.00 E −5 | 7.0 |
| | 2.00 E −5 | 2.0 |
| LDAH | 2.50 E −5 | 0.0 |
| Example 177 | | |
| LDAH | 8.00 E −5 | 50.0 IC |

Accordingly, the present invention also includes a pharmaceutical composition for treating one of the above diseases of conditions comprising an antidisease or anticondition effective amount of a compound of the Formula I as defined above together with a pharmaceutically acceptable carrier.

The present invention further includes a method for treating one of the above named diseases or conditions in mammals, including man, suffering therefrom comprising administering to such mammals either orally or parenterally a corresponding pharmaceutical composition containing a compound of Formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnsium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 1 to 50 mg according to the particular applicatio and the potency of the active ingredient. The compositions can, if desired, also contain other compatible therapeutic agents.

In therapeutic use as described above, the dosages may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

FORMULA

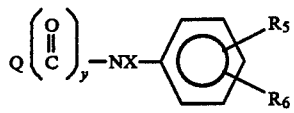   I

FORMULA

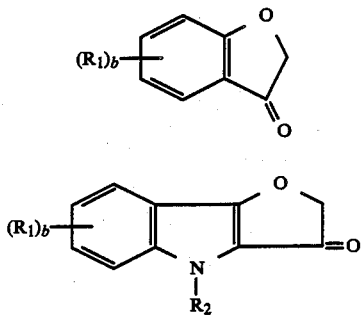   XII₃

XII₆

FORMULA

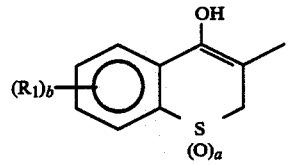   I₁

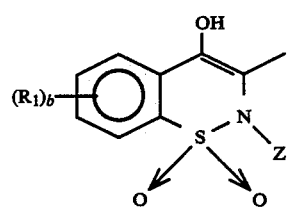   I₂

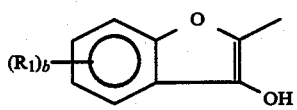   I₃

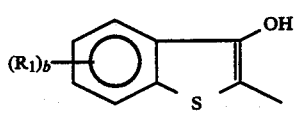   I₄

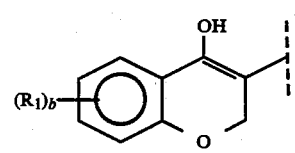   I₅

-continued
FORMULA

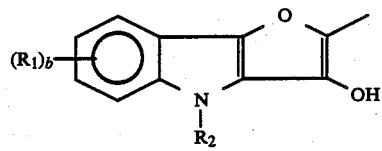   I₆

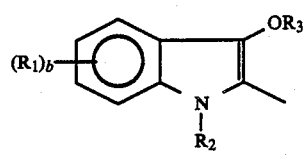   I₇

SCHEME I

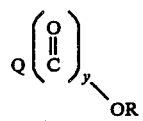

II

+

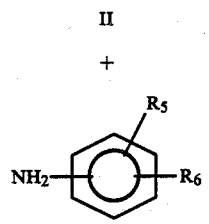

III

↓

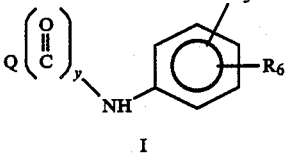

I

SCHEME II

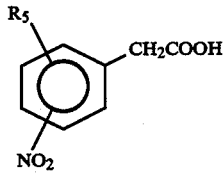

+

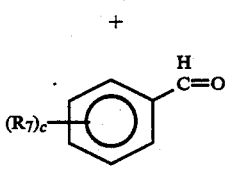

↓

-continued
SCHEME II
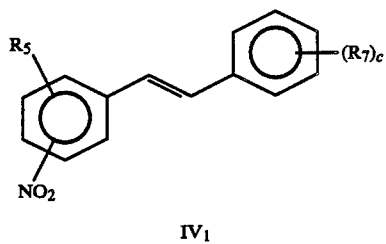
IV₁
SCHEME III
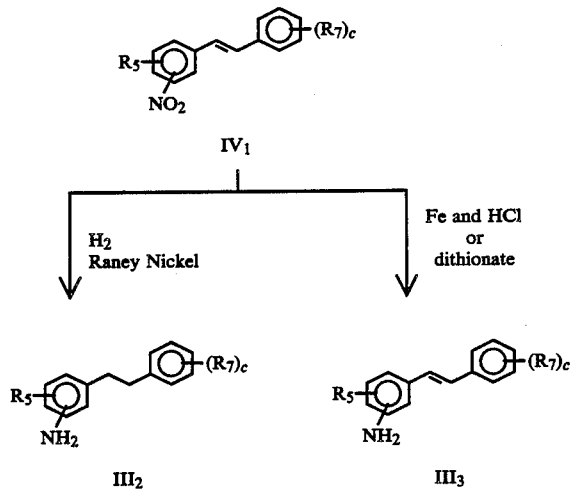
SCHEME IV
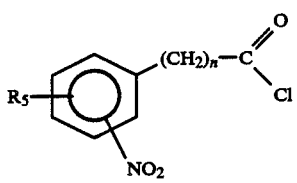
+
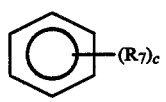
↓ AlCl₃, CH₂Cl₂
-continued
SCHEME IV
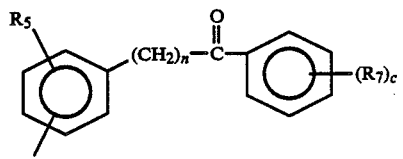
IV₂
↓ H² Pd/C
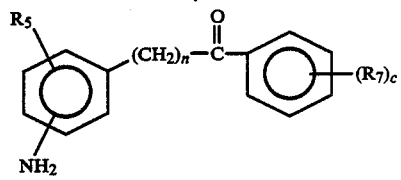
III₄
SCHEME V
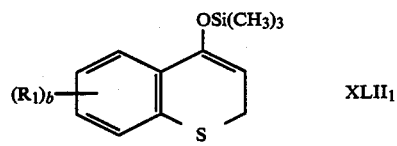  XLII₁
↓
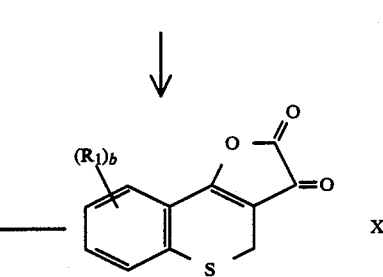  XXXII₁
↓ [O]
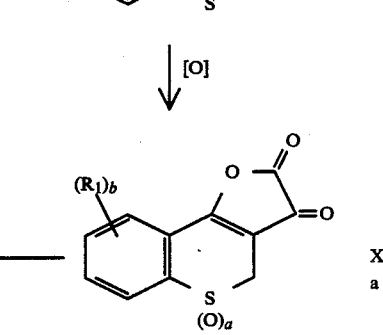  XXII₁/XXII₁
a = 2  a = 1
↓ Esterification
II₁
wherein R is lower alkyl and y = 2

SCHEME VI
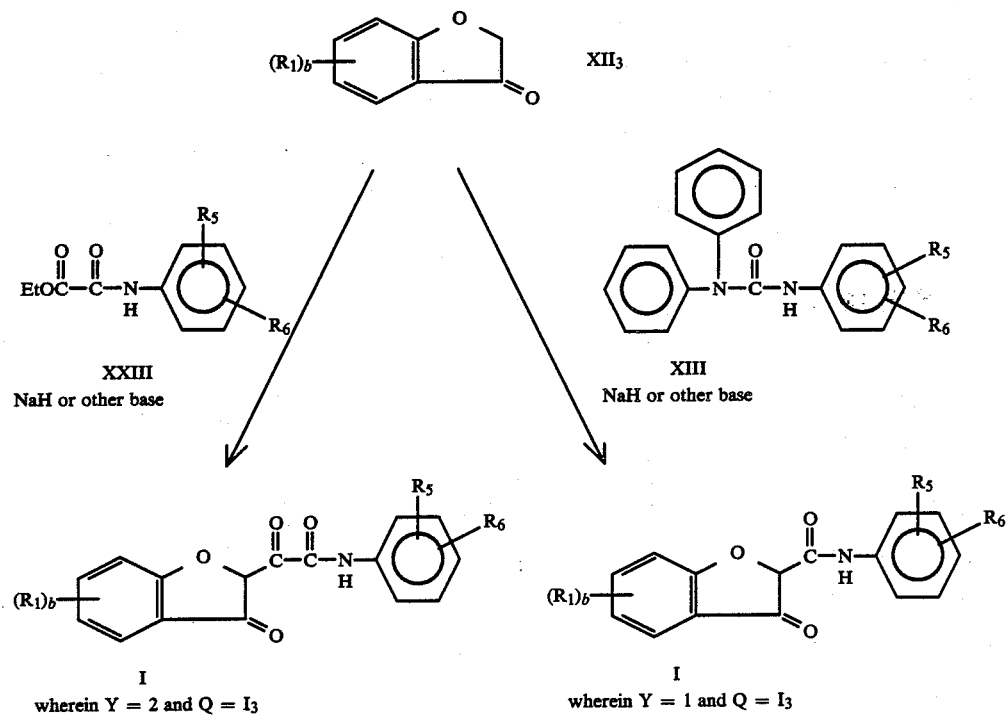
SCHEME VII
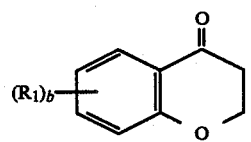
-continued
SCHEME VII
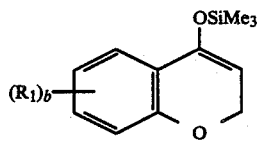
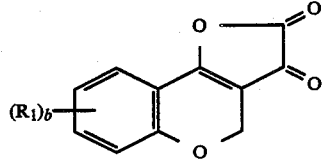
SCHEME VIII
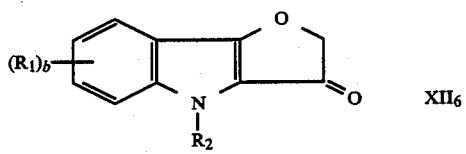

-continued
SCHEME VIII
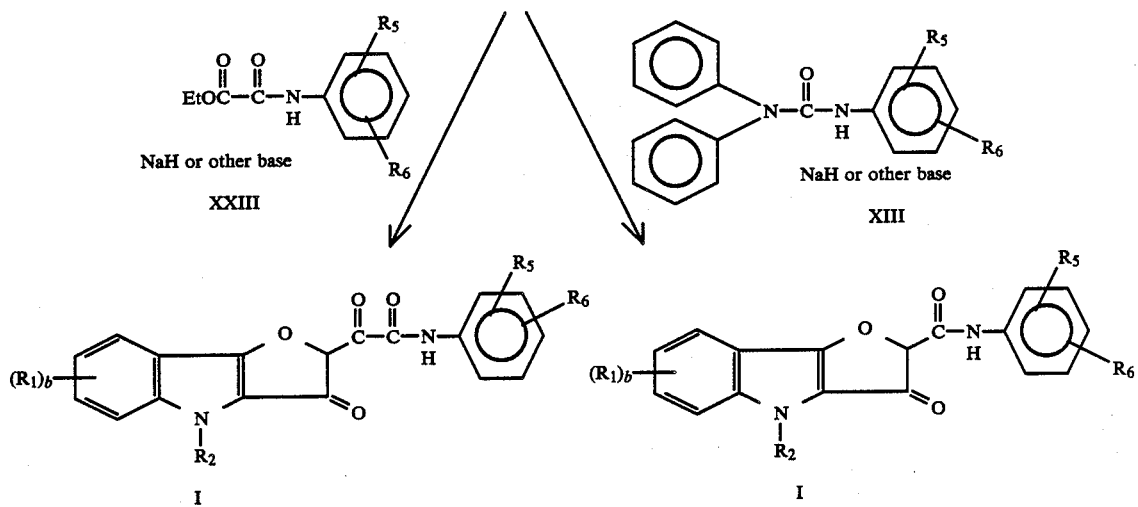
-continued
SCHEME IX
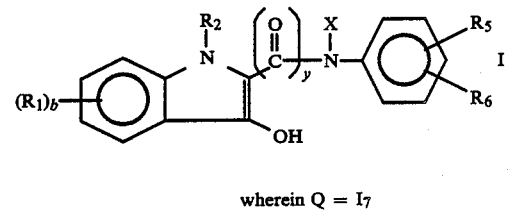
wherein Q = I₇
SCHEME IX
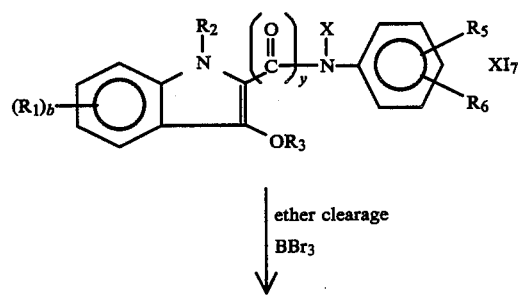
ether cleavage
BBr₃
SCHEME X
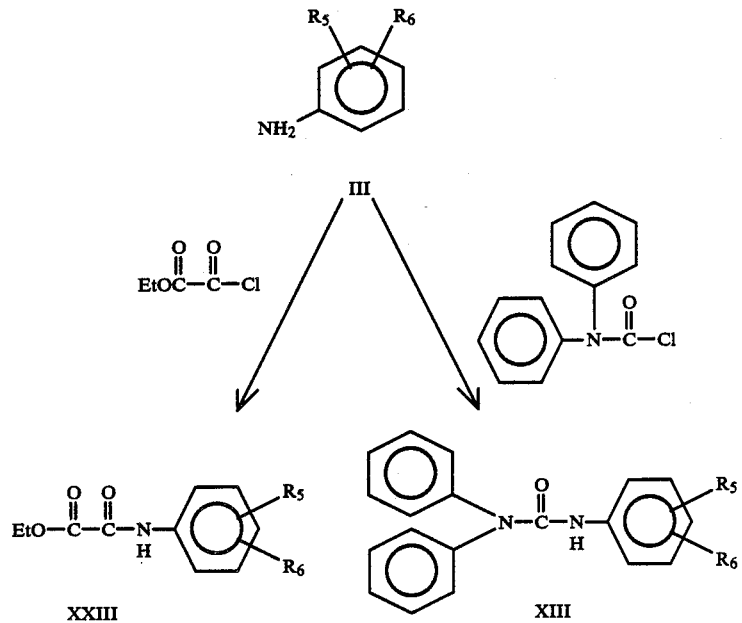
We claim:
1. A compound having the formula

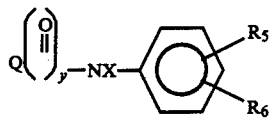

and pharmaceutically acceptable salts thereof, wherein (1) y is one or two; (2) Q is a substituent selected from the group consisting of the formula

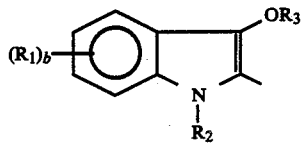

wherein b is zero, one, two, three, or four, X is hydrogen or lower alkyl; $R_1$ may be the same or different if b is two or more, selected from a group consisting of alkyl or from one to four carbons, inclusive; alkoxy of from one to four carbons, inclusive; carboalkoxy or from two to four carbons, inclusive; hydroxy, halogen, nitro, amino, mono- and di-alkylamino having each alkyl the same or different of from one to four carbons inclusive; carbalkoxyamido of from one to four carbons, inclusive; alkysulfonamido of from one to four carbons, inclusive; alkylsulfinyl of from one to four carbons, inclusive; alkylsulfonyl of from one to four carbons, inclusive and —(CH=CH—CH=CH)— taken together with an adjacent ring carbon to form a benzo radical; $R_2$ and $R_3$ are the same or different and or hydrogen, alkyl of from one to six carbons, inclusive; phenyl or benzyl; (3) $R_5$ is hydrogen; alkyl of from one to four carbons, inclusive; alkoxy of from one to four carbons, inclusive; carbalkoxy of from two to four carbons, inclusive; hdyroxy; halogen; or —CH=CH—CH=CH)— taken together with adjacent carbons to form a benzo radical; (4) $R_6$ is alkyl of from six to twenty carbons, —CH=CH—$R_4$, —$(CH_2)_n COR_4$, or —$(CH_2)_n$—$R_4$ wherein n is zero to four, inclusive; and $R_4$ is phenyl optionally substituted at the two through six positions by hydrogen, carboalkoxy, having alkoxy of from one to four carbons, inclusive; alkoxy, or thioalkoxy of from one to four carbons, inclusive; phenalkoxy of from one to four carbons, inclusive; amino, monoalkyl or dialkyl amino having the alkyl of from one to four carbons, inclusive; alkanoylamino of from one to four carbons, inclusive; alkanoylamino of from two to six carbons, inclusive; carboxyl, benzo, halogen, hydroxy, hydroxyalkyl of from one to four carbons inclusive; alkanoyl of from one to four carbons, inclusive; nitro, alkanesulfonamido of from one to four carbons, phenyl.

2. A compound according to claim 1 and being 1H-Indole-2-carboxamide, N-[4-[2-(3,4-dimethoxyphenyl)ethyl]phenyl]-3-methoxy-1-phenyl-.

3. A compound according to claim 1 and being 1H-Indole-2-carboxamide, N-[4-[2-(3,4-dimethoxyphenyl)ethyl]phenyl]-3-methoxy-1-methyl-.

4. A compound according to claim 1 and being 1H-Indole-2-carboxamide, N-[4-[2-(3,4-dimethoxyphenyl)ethyl]phenyl]-N-ethyl-3-methoxy-1-mehtyl-.

5. A compound according to claim 1 and being 1H-Indole-2-carboxamide, N-[4-[2-(3,4-dimethoxyphenyl)ethyl]phenyl]-N-ethyl-3,5-dimethoxy-1-phenyl-.

6. A compound according to claim 1 and being 1H-Indole-2-carboxamide, N-[4-[2-(3,4-dimethoxyphenyl)ethyl]phenyl]-3-methoxy-.

7. A compound according to claim 1 and being 1H-Indole-2-carboxamide, N-[4-[2-(3,4-dimethyoxyphenyl)ethyl]phenyl]-5-methoxy-1-phenyl-3-(phenylmethoxy)-.

8. A compound according to claim 1 and being 1H-Indole-2-carboxamide, N-[4-[2-(3,4-dimethoxyphenyl)ethyl]phenyl]-3,5-dimethoxy-1-phenyl-.

9. A compound according to claim 1 and being 1H-Indole-2-carboxamide, N-[4-[2-(3,4-dimethoxyphenyl)ethyl]phenyl]-3-methoxy-1-(phenylmethyl)-.

10. A compound according to claim 1 and being 1H-Indole-2-acetamide, N-[4-[2-(3,4-dimethoxyphenyl)ethyl]phenyl]-3-hydroxy-5,6-dimethyl-α-oxo-.

11. A compound according to claim 1 and being 1H-Indole-2-carboxamide, N-[4-[2-(3,4-dihydroxyphenyl)ethyl]phenyl]-3-hydroxy-1-methyl-.

12. A compound according to claim 1 and being 1H-Indole-2-acetamide, N-[4-[2-(3,4-dihydroxyphenyl)ethyl]phenyl]-3-hydroxy-5,6-dimethyl-α-oxo-.

13. A compound according to claim 1 and being 1H-Indole-2-carboxamide, N-[4-[2-(3,4-dihydroxyphenyl)ethyl]phenyl]-3-hydroxy-.

14. A compound according to claim 1 and being 1H-Indole-2-acetamide, N-(4-decylphenyl)-3-hydroxy-5,6-dimethyl-α-oxo-.

15. A pharmaceutical composition comprising an antiasthmatic, antiallergic, cardiovascular, antimigraine or antiinflammatory effective amount of a compound as claimed in claim 1 together with a pharmaceutically acceptable carrier.

16. A method for treating asthma, allergy, cardiovascular disease, migraine or inflammation in a mammal suffering therefrom, which comprises administering to said mammal a compound in claim 1.

* * * * *